(12) United States Patent
Miskey et al.

(10) Patent No.: US 7,951,927 B2
(45) Date of Patent: May 31, 2011

(54) RECONSTRUCTED HUMAN MARINER TRANSPOSON CAPABLE OF STABLE GENE TRANSFER INTO CHROMOSOMES IN VERTEBRATES

(75) Inventors: Csaba Miskey, Berlin (DE); Zoltan Ivics, Berlin (DE)

(73) Assignee: Max-Delbrück Centrum für Molekulare Medizin, Berlin (DE)

( * ) Notice: Subject to any disclaimer, the term of this patent is extended or adjusted under 35 U.S.C. 154(b) by 400 days.

(21) Appl. No.: 11/885,856

(22) PCT Filed: Mar. 31, 2006

(86) PCT No.: PCT/EP2006/002976
§ 371 (c)(1),
(2), (4) Date: Sep. 6, 2007

(87) PCT Pub. No.: WO2006/108525
PCT Pub. Date: Oct. 19, 2006

(65) Prior Publication Data
US 2008/0279838 A1 Nov. 13, 2008

(30) Foreign Application Priority Data

Apr. 8, 2005 (EP) ..................................... 05007747

(51) Int. Cl.
*C07H 21/04* (2006.01)
*C12N 15/00* (2006.01)
*C12N 5/00* (2006.01)
*C12N 9/10* (2006.01)

(52) U.S. Cl. .................... 536/23.2; 435/320.1; 435/325; 435/199

(58) Field of Classification Search ......................... None
See application file for complete search history.

(56) References Cited

FOREIGN PATENT DOCUMENTS
WO 2006/108525 10/2006

OTHER PUBLICATIONS

Accession No: QN6H41 Dec. 1, 2001.*
Chica et al. Curr Opin Biotechnol. Aug. 2005;16(4):378-84.*
Witkowski et al. Biochemistry. Sep. 7, 1999; 38(36): 11643-50.*
Seffernick et al. .J Bacteriol. Apr. 2001; 183 (8): 2405-10.*
Meinkoth and Wahl (Current Protocols in Molecular Biology, Hybridization Analysis of DNA Blots, pp. 2.10.8-2.10.11, 1993.*
Liong Zhang, Uma Sankar, David J. Lampe, Hugh M. Robertson and Frank L. Graham, "The Himar1 mariner transposase cloned in a recombinant adenovirus vector is functional in mammalian cells," Nucleic Acids Research, University Press, Surrey, GB, Aug. 1998, vol. 26, No. 16, pp. 3687-3693.
Hugh M. Robertson and Karen L. Zumpano, "Molecular evolution of an ancient mariner transposon, Hsmar1, in the human genome," Gene: An International Journal on Genes and Genomes, Elsevier Science Publishers, Barking, GB, vol. 205, No. 1-2, Dec. 31, 1997, pp. 203-217.
C. Auge-Gouillou, H. Notareschi-Leroy, P. Abad, G. Periquet and Y. Bigot, "Phylogenetic analysis of the functional domains of mariner-like element (MLE) transposases," Molecular & General Genetics: MGG. Nov. 2000, vol. 264, No. 4, Nov. 2000, pp. 506-513.
David J. Lampe, Mair E.A. Churchill and Hugh M. Robertson, "A purified mariner transposase is sufficient to mediate transportation in vitro," Embo Journal, IRL Press, Eynsham, GB, vol. 15, No. 19, 1996, pp. 5470-5479.
Zhang, et al. Nucleic Acids Research, Oxford University Press, Surrey, GB, 26(16): 3687-3693, (1998) XP-000700201.
Robertson, et al. Gene 205(1-2): 203-217 (1997) XP 002156105.
Robertson, et al. Gene 205(1-2):203-217 (1997) XP 002332798.
Auge-Gouillon, et al. Molecular & General Genetics: MGG 264(4): 506-513 (2000) XP002355823.
Lampe, et al. Embo Journal, IRL Press, 15(19):5470-5479 (1996) XP002145182.

* cited by examiner

*Primary Examiner* — Delia M Ramirez
*Assistant Examiner* — Md. Younus Meah
(74) *Attorney, Agent, or Firm* — Klauber & Jackson LLC

(57) ABSTRACT

The present invention refers to a gene transfer system for stably introducing nucleic acid(s) into the DNA of a cell by using a member of the human mariner transposases. The invention further refers to this transposase and to transposons used in the inventive gene transfer system, comprising a nucleic acid sequence with flanking repeats (IRs and/or IR/DRs). Furthermore, applications of this gene transfer system are also disclosed such as gene therapy, insertional mutagenesis, gene discovery (including genome mapping), mobilization of genes, library screening, or functional analysis of genomes in vivo and in vitro. Finally, pharmaceutical compositions and kits are also encompassed.

26 Claims, 10 Drawing Sheets

```
Hsmar1cons.   1 MEMMLDKKQIRAIFLFEFKMGRKAAETTRNINNAFGPGTANERTVQWWFK
Chimp_cl.1    1 MEMMLDKKQIRAIFLFEFKMGRKAAETTRNINNAFGPGTANERTVQWWFK Hsmar1cons   51 KFCKGDESLEDEERSGRPSEVDNDQLRAIIEADPLTTTREVAEELNVDHS
Chimp_cl.1   51 KFCKGDESLEDEERSGRPSEVDNDQLRAIIEADPLTTTREVAEELNVNHS Hsmar1cons  101 TVVRHLKQIGKVKKLDKWVPHELSENQKNRRFEVSSSLILRNNNEPFLDR
Chimp_cl.1  101 TVVRHLKQIGKVKKLDKWVPHELTENQKNRRFEVSSSLILRNRNEPFLDR §
Hsmar1cons  151 IVTCDEKWILYDNRRRPAQWLDREEAPKHFPKPNLHQKKVMVTVWWSAAG
Chimp_cl.1  151 IVTCDEKWILYDNRRRSAQWLDQEEAPKHFSKPILHPKKIMVTIWWSAAG §
Hsmar1cons  201 LIHYSFLNPGETITSEKYAQQIDEMHRKLQRLQPALVNRKGPILLHDNAR
Chimp_cl.1  201 VIHYSFLNPGETITSEKYAQEIDEMHQKLQHLQLALVNRKGPILLHDNAR §
Hsmar1cons  251 PHVAQPTLQKLNELGYEVLPHPPYSPDLSPTDYHFFKHLDNFLQGKRFHN
Chimp_cl.1  251 PHVAQPTLQKLNELGYEVLPHPPYSPDLLPTNYHIFKHLNNFLQGKRFHN Hsmar1cons  301 QQDAENAFQEFVESRSTDFYATGINKLISRWQKCVDCNGSYFD
Chimp_cl.1  301 QQDAENAFQEFVKSRSTDFYATGINQLISRWQKCVDCNGSYFD
```

Fig. 2

```
Hsmar1    1  MEMMLDKKQIRAIFLFEFKMGRKAAETTRNINNAFGPGTANERTVQWWFK
Hcmar1    1  ----MANMKYRYIYEYEFYRGTSAAETARRINNVYGAGAAKESKVRFWFQ
Csmar1    1  ----MDKRQIRTIFLFQFKLGRKAAETARDINDAFGPGTTNERTAQWWFK
Dtmar1    1  ----MEISEIRILMKYEFHRGATTRQAVGNINSVYPTQAVTQTTVAHWFK
Hbmar1    1  IKLKVGKRQIRVIVLYELKLGSKAVETARNINQAFSEGIINKCIAQHCLR

*
Hsmar1   51  KFCK GDESLEDEERSGR PSEVDNDQLRAIIEADPLTTTREVAEELNVDHS
Hcmar1   47  RFRS GIFDLQNQPRGRP EIKVENE--EKAIVADPSQSTSEIAAGFGVSDK
Csmar1   47  KFRG GDESLEDDERSGR PSDVDNDQLRDLVNANTRVTLRELAAELDVTPM
Dtmar1   47  RFRS GDFDMSNQPRSRP EIKVDNDALKADVEADSSQSALELASKFGVAKS
Hbmar1   51  RLRN GDERFEDEEGREC SLVIDDNQL-AIVEVEPCKTTREVVEELNVN-S

*
Hsmar1  101  TVVRHLKQIGKVKKLDKWVPHELSENQKNRRFEVSSSLILRNNNEPFLDR
Hcmar1   95  TVLIYLKQIGKVKKLE-WVPHELSESNLQTRVDCCVTLLNRHNNEGILNR
Csmar1   97  TISNHLKEIGKTKKLDKWVPHELNENQKNRRFEVSSALLLRNNNDPFLDR
Dtmar1   97  IILIHLKQINKVKKLDKWVPHELKDEHKQQRLDACLSLLSRNKADPFLHR
Hbmar1   99  AVVRHLHQVKKSTKLDKWVPQELNEYQKNRRYQICSRFCG-NKNNLFLDC §         *
Hsmar1  151  IVTCDEKWILYDNRRRPAQWLDREEAPKHFPKPNLHQKKVMVTVWWSAAG
Hcmar1  144  IITCDEKWILYDNRKSSQWLNPGDPAKSCPKRKLTQKKLLVSVWWTSAG
Csmar1  147  IVTCDEKWILYDNRRRSAQWLDRDQAPQHFPKPALHQKKVMVTVWWSVAG
Dtmar1  147  IVTCDEKWIMYDNRKSSQWLDPDEPPKHCPKRKVHQKKLMVTVWWSSYG
Hbmar1  148  IVTCDENWILYDNRRRSTQWLDHDEALKHFTKPKLHQKKGMVTVWL-ASE

*              *                       §
Hsmar1  201  LIHYSFLNPGETITSEKYAQQIDEMHRKLQRLQPALVNRKGPILLHDNAR
Hcmar1  194  VVHYSFLKSGQTITADIYCQQLQTMKEELAAKQPRLVNRSRPLLLHDNAR
Csmar1  197  VIHHSFLNPGETITAEIYCQQIDEMHQKLRRMCPRLVNMKGPILLHDNAR
Dtmar1  197  VIHYDFMVPGTSITSDVYCSQLDDMMEKLAIKQPKMFNRLTPILLHDNAR
Hbmar1  197  VIHYNFLCPGETITTEEYCHEIDKVHQELQRLRPALVNRKGPILLHDNAR §
Hsmar1  251  PHVAQPTLQKLNELGYEVLPHPPYSPDLSPTDYHFFKHLDNFLQGKRFHN
Hcmar1  244  PHTAQQTTTKLDELQLECLRHPPYSPDLAPIDYHFFRNLDNFLHGKKFNS
Csmar1  247  PHVAQPTLQKLNQLGYETLPHPAYSPDLSPTDYHFFKHLDNFLREKCFKN
Dtmar1  247  PHSAKNTVAKLQQLGLETLRHPPYSPDLAPTDYHFFQSLDNFLSGKNFTS
Hbmar1  247  PHVSQMTLQKLNELAYETLPYPVYSPDLSSTNYHFLKHFNNLLQEKVSNN Hsmar1  301  QQDAENAFQEFVESRSTDFYATGINKLISRWQKCVDCNGSYFD
Hcmar1  294  YSVVQTAFKEFIDRRPHAFFNKGINELPVRWQKCINNNGAYF-
Csmar1  297  RDDTKNAFNAFVASREPDFYRSGINKLISRWQKCVDCNGAYFD
Dtmar1  297  SGAVKTAFQEFIDSRESVFYTKGLNVLPLKWQQCVDNMGGYFD
Hbmar1  297  KGVTQKAFEEFIGSR-TLFYATGINKLVCCWQCVDYSGSYFD
```

Fig. 3

```
                                              *                      §
Himar1     70  DMRKLCAKWVPRELTFDQKQQRVDDSERCLQLLTRNTPEFFRRYVTMDETWLHHY--
Mpmar1     68  GYRKLCAKWVPRELTIYQKQQRVDDSEACLKLFNHDKKDFLHRYVTMDETWIHHY--
Hsmar2     72  KLSKLSTRWVPKPLRPDQLQTRAELSMEILNKWDQDPEAFLRRIVTGDETWLYQY--
Cemar3a    65  GIKKLMGRFIPHTLTQANLDFLVGDSFSLLIFHGAD--RWLGRLITGNEKWVLYD--
Cbmar1     79  GMRKLFGRFIPHHLTQANLDRRVDDSITLLTLHAGD--RWLDRLITGDEKWVFYD--
Cemar4     68  GMRKILGRFVPHYLTRSNLFHQVDVSYNLLTLHGGD--RWLGRLITENGKWVLYA--
Cbmar2     71  GKVKKVGRYGSHLFAQSNFVSCVGTCLNLLILRCTH--ECS--IITSGDKWVMYD--
Mos1       71  GKIQKVGRWVPHELNERQMERRKNTCEILLSRYKRK--SFLHRIVTGDEKWIFFV--
Momar1     70  --ISKLGRWVPHELSERQKEVRLTVCRELLSRYKNK--SFLYRIITSDEKWIYYD--
Mdmar1     73  GYIQKQGNWVPHELKPRDVERRFCMSEMLLQRHKKK--SFLSRIITGDEKWIHYD--
Demar1     68  GYKKKLDVWVPHDLTQKNLLDRINACDMLLKRNELD--PFLKRMVTGDEKWITYD--
Ammar1     68  GYVQKLDTWVPRELKEKHLTQRINSCDLLKKRNEND--PFLKRLITGDEKWVVYN--
Cmar1      64  GYTLKLDKWVPHQLSEKNKVDRMSTAISLLRRVKNE--PFLDRLLTGDEKWILYN--
Hcmar1     64  GKVKKLE-WVPHELSESNLQTRVDCCVTLLNRHNNE--GILNRIITCDEKWILYD--
Dtmar1     66  NKVKKLDKWVPHELKDEHKQQRLDACLSLLSRNKAD--PFLHRIVTCDEKWIMYD--
Csmar1     66  GKTKKLDKWVPHELNENQKNRRFEVSSALLLRNNND--PFLDRIVTCDEKWILYD--
Hsmar1     70  GKVKKLDKWVPHELSENQKNRRFEVSSSLILRNNNE--PFLDRIVTCDEKWILYD--
Hbmar1     69  KKSTKLDKWVPQELNEYQKNRRYQICSRFCG-NKNN--LFLDCIVTCDENWILYD--
Cemar1     71  GFTSKLGTWVPHELSASQKLTRVNVCTQLLTFRRKF--DWLNNLVTGDEKWVLYV--
Cemar2a    71  GRVEKFGQLVPHNLPDSQKLF-CDLSLSLLTRKRTT--DWVKDIITGNDKWVLYV--
Cemar5     67  GYRRVLARWVPHLFS-FQMQTRETICQSLLLTQQSK--DFLANIVTGDESWLLYN--
Bmmar1     67  G-LAAYKRRTGHFLTDNLKENRVVKSKQLLKRYAKG--GHRKILFTDENFFTIEQHF
Cemar6     62  K-LKAYKKSTCQFLSEAAKIKRKDRAMNLLRRFRNG--AHRKVLFTDEKIFCIEQSF
Cemar9     63  G-LKPYGARKAAILSEKNKLARIQKCKSILAGTRQN--EHLKMLFTDEKLFKVEAEF
C.bG21D19  63  K-MTSYRATKAAILSQANKEKRLIKAKRLLAGTRKK--DHLITIFSDEKLFSVEAEF
Cemar8     63  R-MILYQFQKSAFITDRNKELRLKKQKILLSGTKSG--TLLKTLFKNEK-FIVEAKK
C.bG39007  62  G-LNSYRLLRGQYLTEQSKKNRLEKAKKLLDALKVR--RLSEIIWTDEKIFTVEPLP
consensus      g vkkm kwvph lte qk   rv        ll r      fl rivt dekwily
```

| Version | Mutations | | | | | Activity |
|---|---|---|---|---|---|---|
| | C53R | I139L | P167S | L201V | A219C | |
| *Hsmar1*/1 | X | X | X | 3 | X | no |
| *Hsmar1*/2 | 3 | X | X | X | X | no |
| *Hsmar1*/3 | 3 | X | 3 | X | X | no |
| *Hsmar1*/4 | 3 | X | X | X | 3 | no |
| *Hsmar1*/5 | X | X | 3 | 3 | X | no |
| *Hsmar1*/6 | 3 | X | X | 3 | 3 | no |
| *Hsmar1*/7 | 3 | 3 | 3 | X | X | no |
| *Hsmar1*/8 | 3 | 3 | 3 | 3 | X | no |
| *Hsmar1*/9 | 3 | X | 3 | 3 | 3 | no |
| *Hsmar1*-Prime | 3 | 3 | 3 | 3 | 3 | yes |

B

A

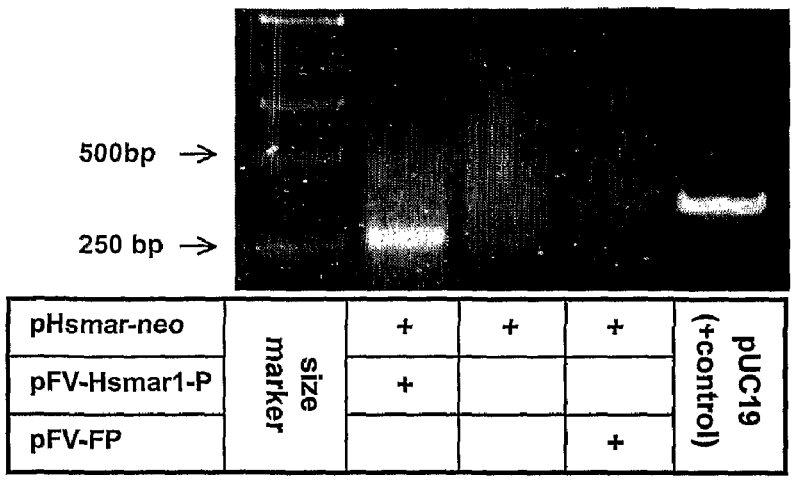

| pHsmar-neo | size marker | + | + | + | pUC19 (+control) |
|---|---|---|---|---|---|
| pFV-Hsmar1-P | | + | | | |
| pFV-FP | | | | + | |

B

*agtgaattcTAttaggtoooHsmar1 TpsonooacctaaTAaagcttggcg*

```
aaacgacggccagtgaattcTATTA TAaagcttggcgtaatcatggtc
aaacgacggccagtgaattcTA---TAaagcttggcgtaatcatggtc
aaacgacggccagtgaattcTA-----aagcttggcgtaatcatggtc
aaa---------------------aagcttggcgtaatcatggtc
aaacgacggcc--------------------------ggtc
------53-bp deletion-----TAaagcttggcgtaatcatggtc
```

C

|  |  | Chr. |
|---|---|---|
| CAGAAACAAGATTTCTTA-*Hsmar1* | Tpson-TAGTTTGTACAATATTTA | 10 |
| CTACATCACAACTATTTA-*Hsmar1* | Tpson-TAGCTCTCATGTTGTAGA | 7 |
| CGTGCAGTTTGTGTGATA-*Hsmar1* | Tpson-TATTTTTTAAAGGAGCTC | 7 |
| GGTAAATATGGATTATTA-*Hsmar1* | Tpson-TAGATTTTCTTAAAAGGA | 7 |
| TCTGTTAGTTCAGTTGTA-*Hsmar1* | Tpson-TAAGAAATGGAGAGCAAA | 7 |
| GTCTTGTGCTGGGAGATA-*Hsmar1* | Tpson-TAGTTATCGCTCCCCGCG | 1 |
| TGACAAAATGGCTACTTA-*Hsmar1* | Tpson-TAAATCCCAAGCAAACTC | 1 |
| AGGTGGGGAGTCGATGTA-*Hsmar1* | Tpson-TACTAGCTTTGGTGCTTT | 1 |

Fig. 8

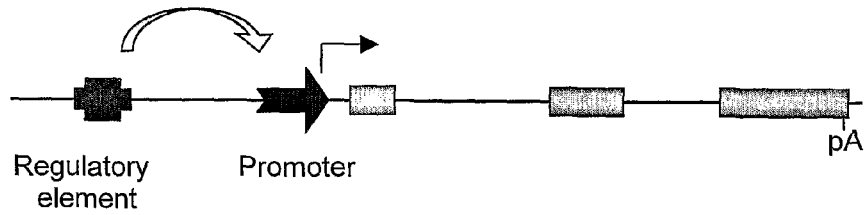
a.
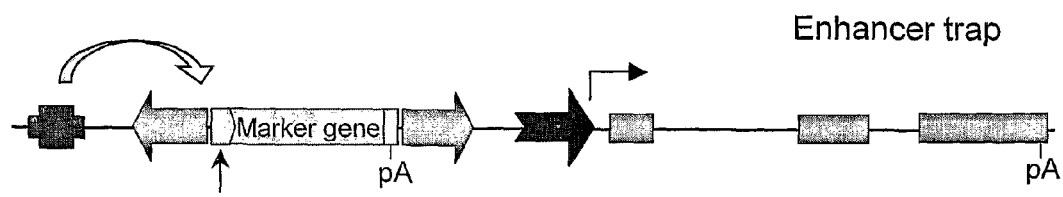
Enhancer trap
b.
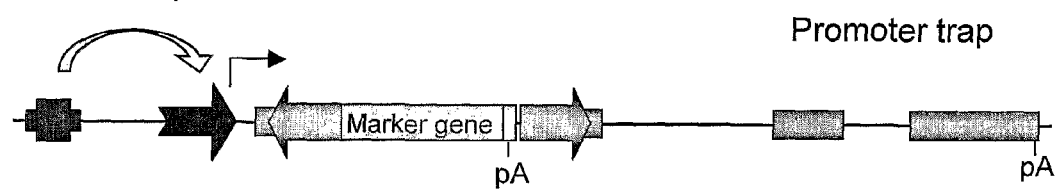
Promoter trap
c.
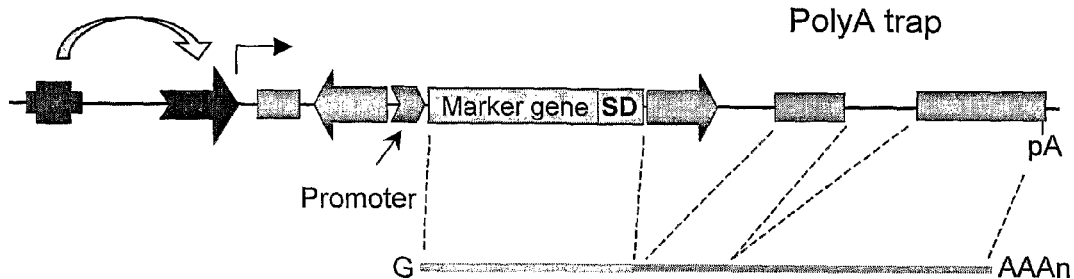
PolyA trap
d.
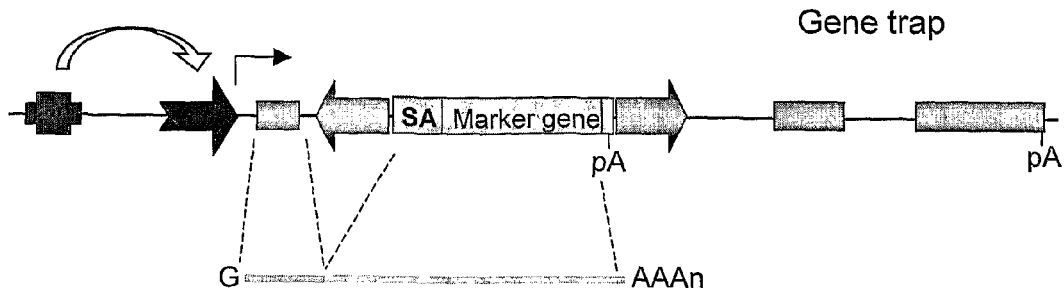
Gene trap
Fig. 10

SEQUENCE LISTING

```
<160> NUMBER OF SEQ ID NOS: 40

<210> SEQ ID NO 1
<211> LENGTH: 343
<212> TYPE: PRT
<213> ORGANISM: Homo sapiens
<220> FEATURE:
<221> NAME/KEY: misc_feature
<223> OTHER INFORMATION: Description of sequence:  Protein sequence of
      Hsmar1-Prime (Hsmar1-P)

<400> SEQUENCE: 1

Met Glu Met Met Leu Asp Lys Lys Gln Ile Arg Ala Ile Phe Leu Phe
1               5                   10                  15

Glu Phe Lys Met Gly Arg Lys Ala Ala Glu Thr Thr Arg Asn Ile Asn
            20                  25                  30

Asn Ala Phe Gly Pro Gly Thr Ala Asn Glu Arg Thr Val Gln Trp Trp
        35                  40                  45

Phe Lys Lys Phe Arg Lys Gly Asp Glu Ser Leu Glu Asp Glu Glu Arg
    50                  55                  60

Ser Gly Arg Pro Ser Glu Val Asp Asn Asp Gln Leu Arg Ala Ile Ile
65                  70                  75                  80

Glu Ala Asp Pro Leu Thr Thr Thr Arg Glu Val Ala Glu Glu Leu Asn
                85                  90                  95

Val Asp His Ser Thr Val Val Arg His Leu Lys Gln Ile Gly Lys Val
            100                 105                 110

Lys Lys Leu Asp Lys Trp Val Pro His Glu Leu Ser Glu Asn Gln Lys
        115                 120                 125

Asn Arg Arg Phe Glu Val Ser Ser Ser Leu Leu Leu Arg Asn Asn Asn
    130                 135                 140

Glu Pro Phe Leu Asp Arg Ile Val Thr Cys Asp Glu Lys Trp Ile Leu
145                 150                 155                 160

Tyr Asp Asn Arg Arg Arg Ser Ala Gln Trp Leu Asp Arg Glu Glu Ala
                165                 170                 175

Pro Lys His Phe Pro Lys Pro Asn Leu His Gln Lys Lys Val Met Val
            180                 185                 190

Thr Val Trp Trp Ser Ala Ala Gly Val Ile His Tyr Ser Phe Leu Asn
        195                 200                 205

Pro Gly Glu Thr Ile Thr Ser Glu Lys Tyr Cys Gln Gln Ile Asp Glu
```

```
                        210                 215                 220
Met His Arg Lys Leu Gln Arg Leu Gln Pro Ala Leu Val Asn Arg Lys
225                 230                 235                 240

Gly Pro Ile Leu Leu His Asp Asn Ala Arg Pro His Val Ala Gln Pro
                245                 250                 255

Thr Leu Gln Lys Leu Asn Glu Leu Gly Tyr Glu Val Leu Pro His Pro
            260                 265                 270

Pro Tyr Ser Pro Asp Leu Ser Pro Thr Asp Tyr His Phe Lys His
        275                 280                 285

Leu Asp Asn Phe Leu Gln Gly Lys Arg Phe His Asn Gln Gln Asp Ala
    290                 295                 300

Glu Asn Ala Phe Gln Glu Phe Val Glu Ser Arg Ser Thr Asp Phe Tyr
305                 310                 315                 320

Ala Thr Gly Ile Asn Lys Leu Ile Ser Arg Trp Gln Lys Cys Val Asp
                325                 330                 335

Cys Asn Gly Ser Tyr Phe Asp
            340

<210> SEQ ID NO 2
<211> LENGTH: 1032
<212> TYPE: DNA
<213> ORGANISM: Homo sapiens
<220> FEATURE:
<221> NAME/KEY: misc_feature
<223> OTHER INFORMATION: Description of sequence: Nucleic acid sequence
      encoding Hsmar1-Prime (Hsmar1-P)
<220> FEATURE:
<221> NAME/KEY: CDS
<222> LOCATION: (1)..(1032)

<400> SEQUENCE: 2 atg gaa atg atg tta gac aaa aag caa att cga gca att ttt tta ttc      48
Met Glu Met Met Leu Asp Lys Lys Gln Ile Arg Ala Ile Phe Leu Phe
1               5                  10                  15 gag ttc aaa atg ggt cgt aaa gca gca gag aca act cgc aac att aac      96
Glu Phe Lys Met Gly Arg Lys Ala Ala Glu Thr Thr Arg Asn Ile Asn
                20                  25                  30 aac gca ttt ggc cca gga act gct aac gaa cgt aca gtg cag tgg tgg     144
Asn Ala Phe Gly Pro Gly Thr Ala Asn Glu Arg Thr Val Gln Trp Trp
            35                  40                  45 ttc aag aag ttt cgc aaa gga gat gag agc ctt gaa gat gag gag cgt     192
Phe Lys Lys Phe Arg Lys Gly Asp Glu Ser Leu Glu Asp Glu Glu Arg
        50                  55                  60 agt ggc cgg cca tca gaa gtt gac aac gac caa ctg aga gca atc atc     240
Ser Gly Arg Pro Ser Glu Val Asp Asn Asp Gln Leu Arg Ala Ile Ile
65                  70                  75                  80 gaa gct gat cct ctt aca act aca aga gaa gtt gcc gaa gaa ctt aat     288
Glu Ala Asp Pro Leu Thr Thr Thr Arg Glu Val Ala Glu Glu Leu Asn
                85                  90                  95 gta gac cat tct aca gtc gtt cgg cat ttg aag caa att gga aag gtg     336
Val Asp His Ser Thr Val Val Arg His Leu Lys Gln Ile Gly Lys Val
            100                 105                 110 aaa aag ctc gat aag tgg gtg cct cat gag ctg agt gaa aat caa aaa     384
Lys Lys Leu Asp Lys Trp Val Pro His Glu Leu Ser Glu Asn Gln Lys
        115                 120                 125 aat cgt cgt ttt gaa gtg tca tct tct ctt ctt cta cgc aac aac aac     432
Asn Arg Arg Phe Glu Val Ser Ser Ser Leu Leu Leu Arg Asn Asn Asn
    130                 135                 140 gaa cca ttt ctc gat cgg att gtg acg tgc gat gaa aag tgg att tta     480
Glu Pro Phe Leu Asp Arg Ile Val Thr Cys Asp Glu Lys Trp Ile Leu
145                 150                 155                 160
```

```
tat gac aac cgg cga cga tca gct cag tgg ttg gat cga gaa gaa gct      528
Tyr Asp Asn Arg Arg Arg Ser Ala Gln Trp Leu Asp Arg Glu Glu Ala
                165                 170                 175 cca aag cac ttc cca aag cca aac ttg cac caa aaa aag gtc atg gtc      576
Pro Lys His Phe Pro Lys Pro Asn Leu His Gln Lys Lys Val Met Val
            180                 185                 190 act gtt tgg tgg tct gct gct ggt gtg atc cac tac agc ttt ctg aat      624
Thr Val Trp Trp Ser Ala Ala Gly Val Ile His Tyr Ser Phe Leu Asn
            195                 200                 205 ccc ggt gaa acc att aca tct gag aag tat tgt cag caa atc gat gag      672
Pro Gly Glu Thr Ile Thr Ser Glu Lys Tyr Cys Gln Gln Ile Asp Glu
        210                 215                 220 atg cac cga aaa ctg caa cgc ctg cag ccg gca ttg gtc aac aga aag      720
Met His Arg Lys Leu Gln Arg Leu Gln Pro Ala Leu Val Asn Arg Lys
225                 230                 235                 240 ggc cca att ctt ctc cac gac aat gcc cga ccg cat gtt gca caa ccc      768
Gly Pro Ile Leu Leu His Asp Asn Ala Arg Pro His Val Ala Gln Pro
                245                 250                 255 aca ctt caa aag ttg aat gaa ttg ggc tat gaa gtt ttg cct cat cca      816
Thr Leu Gln Lys Leu Asn Glu Leu Gly Tyr Glu Val Leu Pro His Pro
            260                 265                 270 ccg tat tca cct gac ctc tcg cca acc gac tac cac ttc ttc aag cat      864
Pro Tyr Ser Pro Asp Leu Ser Pro Thr Asp Tyr His Phe Phe Lys His
            275                 280                 285 ctc gac aac ttt ttg cag gga aaa cgc ttc cac aac caa cag gat gca      912
Leu Asp Asn Phe Leu Gln Gly Lys Arg Phe His Asn Gln Gln Asp Ala
        290                 295                 300 gaa aat gct ttc caa gag ttt gtc gaa tcc cga agc acg gat ttt tac      960
Glu Asn Ala Phe Gln Glu Phe Val Glu Ser Arg Ser Thr Asp Phe Tyr
305                 310                 315                 320 gct aca gga ata aac aaa ctt att tct cgt tgg caa aaa tgt gtt gat     1008
Ala Thr Gly Ile Asn Lys Leu Ile Ser Arg Trp Gln Lys Cys Val Asp
                325                 330                 335 tgt aat ggt tcc tat ttt gat taa                                     1032
Cys Asn Gly Ser Tyr Phe Asp
            340

<210> SEQ ID NO 3
<211> LENGTH: 1287
<212> TYPE: DNA
<213> ORGANISM: Homo sapiens
<220> FEATURE:
<221> NAME/KEY: misc_feature
<223> OTHER INFORMATION: Description of sequence:  Sequence of
      Hsmar1-Prime transposable element
<220> FEATURE:
<221> NAME/KEY: CDS
<222> LOCATION: (179)..(1207)

<400> SEQUENCE: 3
ttaggttggt gcaaaagtaa ttgcggtttt tgcattgttg gaatttgccg tttgatattg       60
gaatacattc ttaaataaat gtggttatgt tatacatcat tttaatgcgc atttctcgct      120
ttacgttttt ttgctaatga cttattactt gctgtttatt ttatgtttat tttagact        178 atg gaa atg atg tta gac aaa aag caa att cga gca att ttt tta ttc      226
Met Glu Met Met Leu Asp Lys Lys Gln Ile Arg Ala Ile Phe Leu Phe
1               5                   10                  15 gag ttc aaa atg ggt cgt aaa gca gca gag aca act cgc aac att aac      274
Glu Phe Lys Met Gly Arg Lys Ala Ala Glu Thr Thr Arg Asn Ile Asn
            20                  25                  30 aac gca ttt ggc cca gga act gct aac gaa cgt aca gtg cag tgg tgg      322
Asn Ala Phe Gly Pro Gly Thr Ala Asn Glu Arg Thr Val Gln Trp Trp
```

|  |  |  |  |  |  |  |  |  |  |  |  |  |  |  |  |
|---|---|---|---|---|---|---|---|---|---|---|---|---|---|---|---|
|  | 35 |  |  |  | 40 |  |  |  |  | 45 |  |  |  |  |  |

```
ttc aag aag ttt cgc aaa gga gat gag agc ctt gaa gat gag gag cgt      370
Phe Lys Lys Phe Arg Lys Gly Asp Glu Ser Leu Glu Asp Glu Glu Arg
 50                  55                  60 agt ggc cgg cca tca gaa gtt gac aac gac caa ctg aga gca atc atc      418
Ser Gly Arg Pro Ser Glu Val Asp Asn Asp Gln Leu Arg Ala Ile Ile
 65                  70                  75                  80 gaa gct gat cct ctt aca act aca aga gaa gtt gcc gaa gaa ctt aat      466
Glu Ala Asp Pro Leu Thr Thr Thr Arg Glu Val Ala Glu Glu Leu Asn
                 85                  90                  95 gta gac cat tct aca gtc gtt cgg cat ttg aag caa att gga aag gtg      514
Val Asp His Ser Thr Val Val Arg His Leu Lys Gln Ile Gly Lys Val
            100                 105                 110 aaa aag ctc gat aag tgg gtg cct cat gag ctg agt gaa aat caa aaa      562
Lys Lys Leu Asp Lys Trp Val Pro His Glu Leu Ser Glu Asn Gln Lys
        115                 120                 125 aat cgt cgt ttt gaa gtg tca tct tct ctt ctt cta cgc aac aac aac      610
Asn Arg Arg Phe Glu Val Ser Ser Ser Leu Leu Leu Arg Asn Asn Asn
130                 135                 140 gaa cca ttt ctc gat cgg att gtg acg tgc gat gaa aag tgg att tta      658
Glu Pro Phe Leu Asp Arg Ile Val Thr Cys Asp Glu Lys Trp Ile Leu
145                 150                 155                 160 tat gac aac cgg cga cga tca gct cag tgg ttg gat cga gaa gaa gct      706
Tyr Asp Asn Arg Arg Arg Ser Ala Gln Trp Leu Asp Arg Glu Glu Ala
                165                 170                 175 cca aag cac ttc cca aag cca aac ttg cac caa aaa aag gtc atg gtc      754
Pro Lys His Phe Pro Lys Pro Asn Leu His Gln Lys Lys Val Met Val
            180                 185                 190 act gtt tgg tgg tct gct gct ggt gtg atc cac tac agc ttt ctg aat      802
Thr Val Trp Trp Ser Ala Ala Gly Val Ile His Tyr Ser Phe Leu Asn
        195                 200                 205 ccc ggt gaa acc att aca tct gag aag tat tgt cag caa atc gat gag      850
Pro Gly Glu Thr Ile Thr Ser Glu Lys Tyr Cys Gln Gln Ile Asp Glu
210                 215                 220 atg cac cga aaa ctg caa cgc ctg cag ccg gca ttg gtc aac aga aag      898
Met His Arg Lys Leu Gln Arg Leu Gln Pro Ala Leu Val Asn Arg Lys
225                 230                 235                 240 ggc cca att ctt ctc cac gac aat gcc cga ccg cat gtt gca caa ccc      946
Gly Pro Ile Leu Leu His Asp Asn Ala Arg Pro His Val Ala Gln Pro
                245                 250                 255 aca ctt caa aag ttg aat gaa ttg ggc tat gaa gtt ttg cct cat cca      994
Thr Leu Gln Lys Leu Asn Glu Leu Gly Tyr Glu Val Leu Pro His Pro
            260                 265                 270 ccg tat tca cct gac ctc tcg cca acc gac tac cac ttc ttc aag cat     1042
Pro Tyr Ser Pro Asp Leu Ser Pro Thr Asp Tyr His Phe Phe Lys His
        275                 280                 285 ctc gac aac ttt ttg cag gga aaa cgc ttc cac aac caa cag gat gca     1090
Leu Asp Asn Phe Leu Gln Gly Lys Arg Phe His Asn Gln Gln Asp Ala
290                 295                 300 gaa aat gct ttc caa gag ttt gtc gaa tcc cga agc acg gat ttt tac     1138
Glu Asn Ala Phe Gln Glu Phe Val Glu Ser Arg Ser Thr Asp Phe Tyr
305                 310                 315                 320 gct aca gga ata aac aaa ctt att tct cgt tgg caa aaa tgt gtt gat     1186
Ala Thr Gly Ile Asn Lys Leu Ile Ser Arg Trp Gln Lys Cys Val Asp
                325                 330                 335 tgt aat ggt tcc tat ttt gat taataaagat gtgtttgagc ctagttataa        1237
Cys Asn Gly Ser Tyr Phe Asp
            340 tgatttaaaa ttcacggtcc aaaaccgcaa ttacttttgc accaacctaa              1287
```

```
<210> SEQ ID NO 4
<211> LENGTH: 30
<212> TYPE: DNA
<213> ORGANISM: Homo sapiens
<220> FEATURE:
<221> NAME/KEY: misc_feature
<223> OTHER INFORMATION: Description of sequence:
      inverted terminal repeat

<400> SEQUENCE: 4
ttaggttggt gcaaaagtaa ttgcggtttt                                  30

<210> SEQ ID NO 5
<211> LENGTH: 30
<212> TYPE: DNA
<213> ORGANISM: Homo sapiens
<220> FEATURE:
<221> NAME/KEY: misc_feature
<223> OTHER INFORMATION: Description of sequence:
      inverted terminal repeat

<400> SEQUENCE: 5
aaaaccgcaa ttactttgc accaacctaa                                   30

<210> SEQ ID NO 6
<211> LENGTH: 178
<212> TYPE: DNA
<213> ORGANISM: Homo sapiens
<220> FEATURE:
<221> NAME/KEY: misc_feature
<223> OTHER INFORMATION: Description of sequence:
      5'UTR of Hsmar1-Prime-Full DNA

<400> SEQUENCE: 6
ttaggttggt gcaaaagtaa ttgcggtttt tgcattgttg gaatttgccg tttgatattg   60
gaatacattc ttaaataaat gtggttatgt tatacatcat tttaatgcgc atttctcgct  120
ttacgttttt ttgctaatga cttattactt gctgtttatt ttatgtttat tttagact    178

<210> SEQ ID NO 7
<211> LENGTH: 77
<212> TYPE: DNA
<213> ORGANISM: Homo sapiens
<220> FEATURE:
<221> NAME/KEY: misc_feature
<223> OTHER INFORMATION: Description of sequence:
      3'UTR of Hsmar1-Prime-Full DNA

<400> SEQUENCE: 7
taaagatgtg tttgagccta gttataatga tttaaaattc acggtccaaa accgcaatta   60
cttttgcacc aacctaa                                                 77

<210> SEQ ID NO 8
<211> LENGTH: 42
<212> TYPE: DNA
<213> ORGANISM: Artificial
<220> FEATURE:
<223> OTHER INFORMATION: Description of sequence: primer Hsmar1-F

<400> SEQUENCE: 8
gactgcggcc gcagactatg gaaatgatgt tagacaaaaa gc                     42

<210> SEQ ID NO 9
<211> LENGTH: 24
<212> TYPE: DNA
<213> ORGANISM: Artificial
<220> FEATURE:
```

```
<223> OTHER INFORMATION: Description of Sequence: primer Hsmar1-F

<400> SEQUENCE: 9
aaaataggaa ccattacaat caac                                          24

<210> SEQ ID NO 10
<211> LENGTH: 26
<212> TYPE: DNA
<213> ORGANISM: Artificial
<220> FEATURE:
<223> OTHER INFORMATION: Description of sequence:
      Primer for transposition assay

<400> SEQUENCE: 10
cagtaagaga attatgcagt gctgcc                                        26

<210> SEQ ID NO 11
<211> LENGTH: 23
<212> TYPE: DNA
<213> ORGANISM: Artificial
<220> FEATURE:
<223> OTHER INFORMATION: Description of sequence:
      Primer for transposition assay

<400> SEQUENCE: 11
cctctgacac atgcagctcc cgg                                           23

<210> SEQ ID NO 12
<211> LENGTH: 25
<212> TYPE: DNA
<213> ORGANISM: Artificial
<220> FEATURE:
<223> OTHER INFORMATION: Description of sequence:
      Primer for transposition assay

<400> SEQUENCE: 12
tctttcctgc gttatcccct gattc                                         25

<210> SEQ ID NO 13
<211> LENGTH: 22
<212> TYPE: DNA
<213> ORGANISM: Artificial
<220> FEATURE:
<223> OTHER INFORMATION: Description of sequence:
      Primer for transposition assay

<400> SEQUENCE: 13
tcacaagctt gtctgtaagc gg                                            22

<210> SEQ ID NO 14
<211> LENGTH: 24
<212> TYPE: DNA
<213> ORGANISM: Artificial
<220> FEATURE:
<223> OTHER INFORMATION: Description of sequence:
      Primer for transposition assay

<400> SEQUENCE: 14
gcgaaagggg gatgtgctgc aagg                                          24

<210> SEQ ID NO 15
<211> LENGTH: 23
<212> TYPE: DNA
<213> ORGANISM: Artificial
<220> FEATURE:
<223> OTHER INFORMATION: Description of sequence:
      Primer for transposition assay
```

```
<400> SEQUENCE: 15
cagctggcac gacaggtttc ccg                                             23

<210> SEQ ID NO 16
<211> LENGTH: 40
<212> TYPE: DNA
<213> ORGANISM: Artificial
<220> FEATURE:
<223> OTHER INFORMATION: Primer for Plasmid rescue of
      integrated Hsmar1 transposons specific for the 5' IR

<400> SEQUENCE: 16
atgatgtata acataaccac atttatttaa gaatgtattc                           40

<210> SEQ ID NO 17
<211> LENGTH: 50
<212> TYPE: DNA
<213> ORGANISM: Artificial
<220> FEATURE:
<223> OTHER INFORMATION: Primer for Plasmid rescue of
      integrated Hsmar1 transposons specific for the 5' IR

<400> SEQUENCE: 17
taaagatgtg tttgagccta gttataatga tttaaaattc acggtccaaa                50

<210> SEQ ID NO 18
<211> LENGTH: 40
<212> TYPE: DNA
<213> ORGANISM: Artificial
<220> FEATURE:
<223> OTHER INFORMATION: Primer for amplification of
      the Hsmar1 transposase gene

<400> SEQUENCE: 18
ctgaactagt ctaatcaaaa taggaaccat tacaatcaac                           40

<210> SEQ ID NO 19
<211> LENGTH: 34
<212> TYPE: DNA
<213> ORGANISM: Artificial
<220> FEATURE:
<223> OTHER INFORMATION: Primer for PCR mutagenesis of
      the Hsmar1 transposase for position S181P

<400> SEQUENCE: 19
gctccaaagc acttcccaaa gccaatcttg cacc                                 34

<210> SEQ ID NO 20
<211> LENGTH: 35
<212> TYPE: DNA
<213> ORGANISM: Artificial
<220> FEATURE:
<223> OTHER INFORMATION: Primer for PCR mutagenesis of
      the Hsmar1 transposase for position E221Q

<400> SEQUENCE: 20
tgagaagtat gctcagcaaa tcgatgagat gcacc                                35

<210> SEQ ID NO 21
<211> LENGTH: 35
<212> TYPE: DNA
<213> ORGANISM: Artificial
<220> FEATURE:
<223> OTHER INFORMATION: Primer for PCR mutagenesis of
      the Hsmar1 transposase for position I285F

<400> SEQUENCE: 21
```
caaccgacta ccacttcttc aagcatctcg acaac         35

<210> SEQ ID NO 22
<211> LENGTH: 33
<212> TYPE: DNA
<213> ORGANISM: Artificial
<220> FEATURE:
<223> OTHER INFORMATION: Primer for PCR mutagenesis of
      the Hsmar1 transposase for position S167P

<400> SEQUENCE: 22
acaaccggcg acgaccagct cagtggttgg atc            33

<210> SEQ ID NO 23
<211> LENGTH: 47
<212> TYPE: DNA
<213> ORGANISM: Artificial
<220> FEATURE:
<223> OTHER INFORMATION: Primer for PCR mutagenesis of
      the Hsmar1 transposase for position I184N+P187Q

<400> SEQUENCE: 23
caaagccaat cttgcaccaa aaaaggtca tggtcactgt ttggtgg    47

<210> SEQ ID NO 24
<211> LENGTH: 44
<212> TYPE: DNA
<213> ORGANISM: Artificial
<220> FEATURE:
<223> OTHER INFORMATION: Primer for PCR mutagenesis of
      the Hsmar1 transposase for position H231R+L234P

<400> SEQUENCE: 24
ccgaaaactg caacgcctgc agccggcatt ggtcaacaga aagg    44

<210> SEQ ID NO 25
<211> LENGTH: 45
<212> TYPE: DNA
<213> ORGANISM: Artificial
<220> FEATURE:
<223> OTHER INFORMATION: Primer for PCR mutagenesis of
      the Hsmar1 transposase for position L279S+N282D

<400> SEQUENCE: 25
cgtattcacc tgacctctcg ccaaccgact accacatctt caagc    45

<210> SEQ ID NO 26
<211> LENGTH: 37
<212> TYPE: DNA
<213> ORGANISM: Artificial
<220> FEATURE:
<223> OTHER INFORMATION: Primer for PCR mutagenesis of
      the Hsmar1 transposase for position N98D

<400> SEQUENCE: 26
gaagaactta atgtagacca ttctacagtc gttcggc          37

<210> SEQ ID NO 27
<211> LENGTH: 38
<212> TYPE: DNA
<213> ORGANISM: Artificial
<220> FEATURE:
<223> OTHER INFORMATION: Primer for PCR mutagenesis of
      the Hsmar1 transposase for position R143N

<400> SEQUENCE: 27
cttattctac gcaacaacaa cgaaccattt ctcgatcg         38

<210> SEQ ID NO 28
<211> LENGTH: 38
<212> TYPE: DNA
<213> ORGANISM: Artificial
<220> FEATURE:
<223> OTHER INFORMATION: Primer for PCR mutagenesis of
the Hsmar1 transposase for position T124S

<400> SEQUENCE: 28
gtgcctcatg agctgagtga aaatcaaaaa aatcgtcg                    38

<210> SEQ ID NO 29
<211> LENGTH: 36
<212> TYPE: DNA
<213> ORGANISM: Artificial
<220> FEATURE:
<223> OTHER INFORMATION: Primer for PCR mutagenesis of
the Hsmar1 transposase for position Q173R

<400> SEQUENCE: 29
cagtggttgg atcgagaaga agctccaaag cacttc                      36

<210> SEQ ID NO 30
<211> LENGTH: 36
<212> TYPE: DNA
<213> ORGANISM: Artificial
<220> FEATURE:
<223> OTHER INFORMATION: Primer for PCR mutagenesis of
the Hsmar1 transposase for position I190V+I194V

<400> SEQUENCE: 30
aaaggtcatg gtcactgttt ggtggtctgc tgctgg                      36

<210> SEQ ID NO 31
<211> LENGTH: 31
<212> TYPE: DNA
<213> ORGANISM: Artificial
<220> FEATURE:
<223> OTHER INFORMATION: Primer for PCR mutagenesis of
the Hsmar1 transposase for position V201L

<400> SEQUENCE: 31
tctgctgctg gtctgatcca ctacagcttt c                           31

<210> SEQ ID NO 32
<211> LENGTH: 35
<212> TYPE: DNA
<213> ORGANISM: Artificial
<220> FEATURE:
<223> OTHER INFORMATION: Primer for PCR mutagenesis of
the Hsmar1 transposase for position Q227R

<400> SEQUENCE: 32
tcgatgagat gcaccgaaaa ctgcaacacc tgcag                       35

<210> SEQ ID NO 33
<211> LENGTH: 33
<212> TYPE: DNA
<213> ORGANISM: Artificial
<220> FEATURE:
<223> OTHER INFORMATION: Primer for PCR mutagenesis of
the Hsmar1 transposase for position N290D

<400> SEQUENCE: 33
catcttcaag catctcgaca acttttttgca ggg                        33

<210> SEQ ID NO 34

-continued

```
<211> LENGTH: 38
<212> TYPE: DNA
<213> ORGANISM: Artificial
<220> FEATURE:
<223> OTHER INFORMATION: Primer for PCR mutagenesis of
      the Hsmar1 transposase for position Q326K

<400> SEQUENCE: 34
ttacgctaca ggaataaaca aacttatttc tcgttggc                              38

<210> SEQ ID NO 35
<211> LENGTH: 33
<212> TYPE: DNA
<213> ORGANISM: Artificial
<220> FEATURE:
<223> OTHER INFORMATION: Primer for PCR mutagenesis of
      the Hsmar1 transposase for position K313E

<400> SEQUENCE: 35
ctttccaaga gtttgtcgaa tcccgaagca cgg                                   33

<210> SEQ ID NO 36
<211> LENGTH: 41
<212> TYPE: DNA
<213> ORGANISM: Artificial
<220> FEATURE:
<223> OTHER INFORMATION: Primer for PCR mutagenesis of
      the Hsmar1 transposase for position C53R

<400> SEQUENCE: 36
gtggttcaag aagtttcgca aaggagatga gagccttgaa g                         41

<210> SEQ ID NO 37
<211> LENGTH: 36
<212> TYPE: DNA
<213> ORGANISM: Artificial
<220> FEATURE:
<223> OTHER INFORMATION: Primer for PCR mutagenesis of
      the Hsmar1 transposase for position P167S

<400> SEQUENCE: 37
acaaccggcg acgatcagct cagtggttgg atcgag                               36

<210> SEQ ID NO 38
<211> LENGTH: 39
<212> TYPE: DNA
<213> ORGANISM: Artificial
<220> FEATURE:
<223> OTHER INFORMATION: Primer for PCR mutagenesis of
      the Hsmar1 transposase for position L201V

<400> SEQUENCE: 38
tctgctgctg gtgtgatcca ctacagcttt ctgaatccc                            39

<210> SEQ ID NO 39
<211> LENGTH: 45
<212> TYPE: DNA
<213> ORGANISM: Artificial
<220> FEATURE:
<223> OTHER INFORMATION: Primer for PCR mutagenesis of
      the Hsmar1 transposase for position A219C

<400> SEQUENCE: 39
ccattacatc tgagaagtat tgtcagcaaa tcgatgagat gcacc                     45

<210> SEQ ID NO 40
<211> LENGTH: 45
<212> TYPE: DNA
```

```
<213> ORGANISM: Artificial
<220> FEATURE:
<223> OTHER INFORMATION: Primer for PCR mutagenesis of
      the Hsmar1 transposase for position I139L

<400> SEQUENCE: 40
aagtgtcatc ttctcttctt ctacgcaaca acaacgaacc atttc                    45
```

RECONSTRUCTED HUMAN MARINER TRANSPOSON CAPABLE OF STABLE GENE TRANSFER INTO CHROMOSOMES IN VERTEBRATES

CROSS REFERENCE TO RELATED APPLICATIONS

The present application is a National Stage Application claiming the priority of co-pending PCT Application No. PCT/EP2006/002976 filed Mar. 31, 2006, which in turn, claims priority from European Patent Application Serial No. EP 05007747.8, filed Apr. 8, 2005. Applicants claim the benefits of 35 U.S.C. §120 as to the PCT application and priority under 35 U.S.C. §119 as to the said European application, and the entire disclosures of both applications are incorporated herein by reference in their entireties.

The present invention refers to a gene transfer system for stably introducing nucleic acid(s) into the DNA of a cell by using a member of the human mariner transposases. The invention further refers to this transposase and to transposons used in the inventive gene transfer system, comprising a nucleic acid sequence with flanking repeats (IRs and/or RSDs). Furthermore, applications of this gene transfer system are also disclosed such as gene therapy, insertional mutagenesis, gene discovery (including genome mapping), mobilization of genes, library screening, or functional analysis of genomes in vivo and in vitro. Finally, pharmaceutical compositions and kits are also encompassed.

In the era of functional genomics, there is a sore need for developing efficient means to explore the roles of genes in different cellular functions and, if necessary, to provide effective means for adequately modulating these genes in vitro and in vivo. Such methods, apart others, particularly comprise methods for introducing DNA into a cell.

Typical methods for introducing DNA into a cell include DNA condensing reagents such as calcium phosphate, polyethylene glycol, and the like, lipid-containing reagents, such as liposomes, multi-lamellar vesicles, and the like, as well as virus-mediated strategies. However, these methods all have their limitations. For example, there are size constraints associated with DNA condensing reagents and virus-mediated strategies. Further, the amount of nucleic acid that can be transfected into a cell is limited in virus strategies. Not all methods facilitate insertion of the delivered nucleic acid into cellular nucleic acid and while DNA condensing methods and lipid-containing reagents are relatively easy to prepare, the insertion of nucleic acid into viral vectors can be labor intensive. Moreover, virus-mediated strategies can be cell-type or tissue-type specific and the use of virus-mediated strategies can create immunologic problems when used in vivo.

One suitable tool in order to overcome these problems are transposons. Transposons or transposable elements include a (short) nucleic acid sequence with terminal repeat sequences upstream and downstream thereof. Active transposons encode enzymes that facilitate the excision and insertion of the nucleic acid into target DNA sequences.

At present, two classes of transposons are known, i.e. class I and class II transposons.

Class I transposons, also called retrotransposons or retroposons, include retroviral-like retrotransposons and non-retroviral-like retrotransposons. They work by copying themselves and pasting copies back into the genome in multiple places. Initially, retrotransposons copy themselves to RNA (transcription) but, instead of being translated, the RNA is copied into DNA by a reverse transcriptase (often coded by the transposon itself) and inserted back into the genome. Typical representatives of class I transposons include e.g. Copia (*Drosophila*), Ty1 (yeast), THE-1 (human), Bs1 (maize), the F-element, L1 (human) or Cin4 (maize).

Class II transposons, also called "DNA-only transposons", move by a cut and paste mechanism, rather than by copy and paste, and use the transposase enzyme in this mechanism. Different types of transposase may work in different ways. Some can bind to any part of the DNA molecule, and the target site can be located at any position, while others bind to specific sequences. The transposase then cuts the target site to produce sticky ends, releases the transposon and ligates it into the target site. Typical class II representatives include the P element (*Drosophila*), Ac-Ds (maize), TN3 and IS1 (*E. coli*), Tam3 (snapdragon) etc.

Particularly, with class II transposons, the element-encoded transposase catalyzes the excision of the transposon from its original location and promotes its insertion elsewhere in the genome (Plasterk, 1996 Curr. Top. Microbiol. Immunol. 204, 125-143). Autonomous members of a transposon family can express an active transposase, the transacting factor for transposition, and thus are capable of transposing on their own. Nonautonomous elements have mutated transposase genes but may retain cis-acting DNA sequences. These cis-acting DNA sequences are also referred to as inverted terminal repeats (IR). Some inverted repeat sequences may include one or more direct repeat sequences. These sequences usually are embedded in the terminal inverted repeats (IRs) of the elements, which are required for mobilization in the presence of a complementary transposase from another element. Not a single autonomous element has been isolated from vertebrates so far with the exception of Tol2 (see below); all transposon-like sequences are defective, apparently as a result of a process called "vertical inactivation" (Lohe et al., 1995 Mol. Biol. Evol. 12, 62-72). According to one phylogenetic model (Hartl et al., 1997 Trends Genet. 13, 197-201), the ratio of nonautonomous to autonomous elements in eukaryotic genomes increases as a result of the trans-complementary nature of transposition. This process leads to a state where the ultimate disappearance of active, transposase-producing copies in a genome is inevitable. Consequently, DNA-transposons can be viewed as transitory components of genomes which, in order to avoid extinction, must find ways to establish themselves in a new host. Indeed, horizontal gene transmission between species is thought to be one of the important processes in the evolution of transposons (Lohe et al., 1995 supra and Kidwell, 1992. Curr. Opin. Genet Dev. 2, 868-873).

The natural process of horizontal gene transfer can be mimicked under laboratory conditions. In plants, transposons of the Ac/Ds and Spm families have been routinely transfected into heterologous species (Osborne and Baker, 1995 Curr. Opin. Cell Biol. 7, 406-413). In animals, however, a major obstacle to the transfer of an active transposon system from one species to another has been that of species-specificity of transposition due to the requirement for factors produced by the natural host.

Transposon systems as discussed above may occur in vertebrate and invertebrate systems. In vertebrates, the discovery of DNA-transposons, mobile elements that move via a DNA intermediate, is relatively recent (Radice, A. D., et al., 1994. Mol. Gen. Genet. 244, 606-612). Since then, inactive, highly mutated members of the Tc1/mariner as well as the hAT (hobo/Ac/Tam) superfamilies of eukaryotic transposons have been isolated from different fish species, *Xenopus* and human genomes (Oosumi et al., 1995. Nature 378, 873; Ivics et al. 1995. Mol. Gen. Genet. 247, 312-322; Koga et al., 1996.

Nature 383, 30; Lam et al., 1996. J. Mol. Biol. 257, 359-366 and Lam, W. L., et al. Proc. Natl. Acad. Sci. USA 93, 10870-10875).

Both invertebrate and vertebrate transposons hold potential for transgenesis and insertional mutagenesis in model organisms. Particularly, the availability of alternative transposon systems in the same species opens up new possibilities for genetic analyses. For example, piggyBac transposons can be mobilized in *Drosophila* in the presence of stably inserted P elements (Hacker et al., (2003), Proc Natl Acad Sci USA 100, 7720-5). Because P element- and piggyBac-based systems show different insertion site preferences (Spradling et al. (1995), Proc Natl Acad Sci USA 92, 10824-30, Hacker et al., (2003), Proc Natl Acad Sci USA 100, 7720-5), the number of fly genes that can be insertionally inactivated by transposons can greatly be increased. P element vectors have also been used to insert components of the mariner transposon into the *D. melanogaster* genome by stable germline transformation. In these transgenic flies, mariner transposition can be studied without accidental mobilization of P elements (Lohe and Hartl, (2002), Genetics 160, 519-26).

In vertebrates, three active transposons are currently known and used: the Tol2 element in medaka, and the reconstructed transposons Sleeping Beauty (SB) and Frog Prince (FP).

The Tol2 element is an active member of the hAT transposon family in medaka. It was discovered by a recessive mutation causing an albino phenotype of the Japanese medaka (*Oryzias latipes*), a small freshwater fish of East Asia. It was found that the mutation is due to a 4.7-kb long TE insertion into the fifth exon of the tyrosinase gene. The DNA sequence of the element, named Tol2, is similar to transposons of the hAT family, including hobo of *Drosophila*, Ac of maize and Tam3 of snapdragon.

Sleeping Beauty (SB) is a Tc1/mariner-like element from fish and exhibits high transpositional activity in a variety of vertebrate cultured cell lines, embryonic stem cells and in both somatic and germ line cells of the mouse in vivo.

Also Frog Prince (FP) is a Tc1/mariner-like element that was recently reactivated from genomic transposon copies of the Northern Leopard Frog (*Rana pipiens*). An open reading frame trapping method was used to identify uninterrupted transposase coding regions, and the majority rule consensus of these sequences revealed an active transposase gene. Thus, in contrast to the "resurrection" procedure of SB, the relatively young state of genomic elements in *Rana pipiens* made it possible to ground the majority rule consensus on transposon copies derived from a single species. The SB and FP transposons are clearly distinct, sharing only ~50% identity in their transposase sequences.

Mariner transposons also occur in humans and are represented by two elements, Hsmar1 (Auge-Gouillou, C., Bigot, Y., Pollet, N., Hamelin, M. H., Meunier-Rotival, M. & Periquet, G. (1995). Human and other mammalian genomes contain transposons of the mariner family. FEBS Lett 368, 541-6) and Hsmar2 (Robertson et al., 1996). Hsmar1 entered the human genome lineage approximately 50 Myr ago and increased its copy number up to a few hundred. Transposition of Hsmar1 was ongoing until at least 37 Myr ago, however, none of the present copies encodes for a functional transposase protein due to early stop codons, indels and missense mutation in the transposase genes. A confident consensus sequence of Hsmar1 cDNA clones and of genomic copies was constructed by Robertson and Zumpano (Robertson, H. M. & Zumpano, K. L. (1997). Molecular evolution of an ancient mariner transposon, Hsmar1, in the human genome. Gene 205, 203-17). This consensus is 1287 bp long, has 30 bp perfect IRs, and encodes for a 343 amino acid transposase.

Transposons as the above, particularly Tol2, SB and FP, do not interact and thus may be used as a genetic tool in the presence of others, which considerably broadens the utility of these elements. The preferences of these transposons to insert into expressed genes versus non-coding DNA, and preferences for insertion sites within genes may be substantially different. If so, different patterns of insertion of these transposon systems can be exploited in a complementary fashion. For instance, one could use different transposon systems to transfect several transgenes into cells sequentially, without accidental and unwanted mobilization of already inserted transgenes. In addition, the number of target loci that can be mutagenized by transposon vectors could dramatically increase by combining different transposon systems in genome-wide screens.

In addition to the variation in transpositional activity in hosts, and differences in target site specificity, distinct structural properties of various elements could also be advantageous in certain applications. For example, transposon insertions can be utilized to misexpress genes and to look for gain-of-function phenotypes Rorth, P. (1996, A modular misexpression screen in *Drosophila* detecting tissue-specific phenotypes. Proc Natl Acad Sci USA 93, 12418-22) used a modified P element transposon that carried an inducible promoter directed out from the element to force expression of host genes near to transposon insertion sites and detected tissue specific phenotypes. A prerequisite of such an experimental setup is that the transposon IRs allow read through transcription/translation across the IRs.

Unfortunately, the most active DNA transposons in vertebrates (Minos, S B, F P) all belong to IR/DR-type element with approximately 250 bp long IRs. Such long IR/DR-type elements seriously complicate handling of these constructs and diminishes their application in vivo as well as in vitro due to their less efficient transcription/translation across the IRs. Furthermore, less efficient transcription/translation across the IRs also lowers reliability and effectiveness of gene transfer methods and therapies as well as of experimental results based on use of these transposons.

Thus, there still remains a need for new methods for introducing DNA into a cell, particularly methods that promote the efficient insertion of transposons of varying sizes into the nucleic acid of a cell or the insertion of DNA into the genome of a cell while allowing more efficient transcription/translation results than constructs as available in the state of the art.

The object underlying the present invention is solved by a human mariner transposase selected from one of the following sequences:
a) protein sequence of Hsmar1-Prime as shown by SEQ ID NO: 1;
b) a protein sequence having at least 75% sequence identity to a sequence according to a), wherein following amino acids with respect to SEQ ID NO: 1 remain unaltered:
  i) Arginine at amino acid position 53;
  ii) Lysine at amino acid position 139;
  iii) Serine at amino acid position 167;
  iv) Valine at amino acid position 201;
  v) Cysteine at amino acid position 219.

In a preferred embodiment of the inventive human mariner transposase, the transposase has a protein sequence showing at least 80%, preferably at least 85%, more preferably at least 90%, even more preferably at least 95% and most preferably at least 98% sequence identity with the protein sequence of Hsmar1-Prime as shown by SEQ ID NO: 1, wherein following amino acids with respect to SEQ ID NO: 1 remain unaltered:
  i) Arginine at amino acid position 53;
  ii) Lysine at amino acid position 139;
  iii) Serine at amino acid position 167;
  iv) Valine at amino acid position 201;
  v) Cysteine at amino acid position 219.

In the present invention the term "identity" shall be understood as the degree of identity between two or more proteins, nucleic acids, etc., which may be determined by comparing these sequences using known methods such as computer based sequence alignments (basic local alignment search tool, S. F. Altschul et al., J. Mol. Biol. 215 (1990), 403-410). Such methods include without being limited thereto the GAG programme, including GAP (Devereux, J., et al., *Nucleic Acids Research* 12 (12): 287 (1984); Genetics Computer Group University of Wisconsin, Madison, (WI)); BLASTP or BLASTN, and FASTA (Altschul, S., et al., J. Mol. Biol. 215:403-410) (1999)). Additionally, the Smith Waterman-algorithm may be used to determine the degree of identity between two sequences.

Inventive human mariner transposases showing a sequence identity to SEQ ID NO: 1 as defined above are preferably functional derivatives of the inventive human mariner transposase as represented by SEQ ID NO: 1. Functional derivatives according to the present invention preferably maintain the biological function of the inventive human mariner transposase, i.e. the transposase activity including its binding activity to its IR and/or RSD elements, the excision of the nucleic acid sequence between these IR and/or RSD elements and its insertion activity concerning the excised sequences into specific target sequences. Functional derivatives according to the present invention may comprise one or more amino acid insertion(s), deletion(s) and/or substitution(s) of the inventive human mariner transposase as shown by SEQ ID NO: 1.

Amino acid substitutions in inventive human mariner transposases are preferably conservative amino acid substitutions, which do not alter the biological activity of the inventive human mariner transposase protein. Conservative amino acid substitutions are characterized in that an amino acid belonging to a group of amino acids having a particular size or characteristic can be substituted for another amino acid, particularly in regions of the inventive protein that are not associated with catalytic activity or DNA binding activity, for example. Other amino acid sequences of the inventive human mariner transposase protein include amino acid sequences containing conservative changes that do not significantly alter the activity or binding characteristics of the resulting transposase. Substitutions for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Particularly preferred conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$.

Amino acid insertions and substitutions are preferably carried out at those sequence positions of inventive human mariner transposases according to SEQ ID NO: 1, which do not alter the spatial structure or which relate to the catalytic center or binding region thereof. A change of a spatial structure by insertion(s) or deletion(s) can be detected readily with the aid of, for example, CD spectra (circular dichroism spectra) (Urry, 1985, Absorption, circular Dichroism and ORD of Polypeptides, in: Modern Physical Methods in Biochemistry, Neuberger et al. (Ed.), Elsevier, Amsterdam). Suitable methods for generating proteins with amino acid sequences which contain substitutions in comparison with the native sequence(s) are disclosed for example in the publications U.S. Pat. No. 4,737,462, U.S. Pat. No. 4,588,585, U.S. Pat. No. 4,959,314, U.S. Pat. No. 5,116,943, U.S. Pat. No. 4,879,111 and U.S. Pat. No. 5,017,691. The generation of derivatives is described in particular e.g. by Sambrook et al, (1989, Molecular Cloning: A Laboratory Manual, Cold Spring Harbor Laboratory Press). Other functional derivatives according to the present invention may be in particular those human mariner transposases as defined above which are additionally stabilized in order to avoid physiological degradation. Such stabilization may be obtained by stabilizing the protein backbone by a substitution of by stabilizing the protein backbone by substitution of the amide-type bond, for example also by employing [beta]-amino acids.

The inventive transposase, preferably in combination with an inventive transposon as defined below, has several advantages compared to approaches in the prior art, e.g. with respect to viral and retroviral methods. For example, unlike proviral insertions, transposon insertions can be (re)mobilized by supplying the transposase activity in trans. Thus, instead of performing time-consuming microinjections, it is possible according to the present invention to generate transposon insertions at new loci.

Another embodiment of the present invention refers to nucleic acids encoding an inventive human mariner transposase as defined above. Nucleic acids according to the present invention typically comprise ribonucleic acids, including mRNA, DNA, cDNA, chromosomal DNA, extra-chromosomal DNA, plasmid DNA, viral DNA or RNA. An inventive nucleic acid is preferably selected from any nucleic sequence encoding the same amino acid sequence of an inventive native human mariner transposase protein due to degeneration of its genetic code. These alternative nucleic acid sequences may lead to an improved expression of the encoded fusion protein in a selected host organism. Tables for appropriately adjusting a nucleic acid sequence are known to a skilled person. Preparation and purification of such nucleic acids and/or derivatives are usually carried out by standard procedures (see Sambrook et al. 2001, Molecular Cloning: A Laboratory Manual, Cold Spring Harbor, N.Y.). Other variants of these native nucleic acids may have one or more codon(s) inserted, deleted and/or substituted as compared to native nucleic acid sequences. These sequence variants preferably lead to inventive human mariner transposase proteins having at least one amino acid substituted, deleted and/or inserted as compared to the native nucleic acid sequences of inventive human mariner transposases. Therefore, inventive nucleic acid sequences may code for modified (non-natural) human mariner transposase sequences. Further, promoters or other expression control regions can be operably linked with the nucleic acid encoding the inventive human mariner transposase protein to regulate expression of the protein in a quantitative or in a tissue-specific manner.

In a particularly preferred embodiment, the nucleic acid sequence encoding an inventive human mariner transposon protein comprises the sequence as shown in SEQ ID NO: 2. In a further embodiment of the nucleic acid encoding the inventive human mariner transposase, has a nucleic acid sequence showing at least 75% or 80%, preferably at least 85%, more preferably at least 90%, even more preferably at least 95% and most preferably at least 98% sequence identity with the nucleic acid sequence SEQ ID NO: 2. Nevertheless, any of these have to encode the following amino acids (as referred to the non-altered amino acid sequence of SEQ ID NO: 1), whatever the underlying nucleic acid sequence is.

i) Arginine at amino acid position 53;
ii) Lysine at amino acid position 139;
iii) Serine at amino acid position 167;
iv) Valine at amino acid position 201;
v) Cysteine at amino acid position 219.

In another preferred embodiment the inventive nucleic acid encoding the inventive transposase is selected from a nucleic acid sequence encoding the inventive human mariner transposase as defined above and being capable of hybridizing to a complement of a nucleic acid sequence as defined above under stringent conditions. Stringent conditions are e.g. the following hybridization conditions: 30% (v/v) formamide in 0.5*SSC, 0.1% (w/v) SDS at 42° C. for 7 hours.

The inventive human mariner transposase protein as defined above can be transfected into a cell as a protein or as ribonucleic acid, including mRNA, as DNA, e.g. as extrachromosomal DNA including, but not limited to, episomal DNA, as plasmid DNA, or as viral nucleic acid. Furthermore, the inventive nucleic acid encoding the inventive human mariner transposase protein can be transfected into a cell as a nucleic acid vector such as a plasmid, or as a gene expression vector, including a viral vector. Therefore, the nucleic acid can be circular or linear. A vector, as used herein, refers to a plasmid, a viral vector or a cosmid that can incorporate nucleic acid encoding the Human mariner transposase protein or the transposon of this invention. The terms "coding sequence" or "open reading frame" refer to a region of nucleic acid that can be transcribed and/or translated into a polypeptide in vivo when placed under the control of the appropriate regulatory sequences.

DNA encoding the inventive human mariner transposase protein can be stably inserted into the genome of the cell or into a vector for constitutive or inducible expression. Where the inventive human mariner transposase protein is transfected into the cell or inserted into the vector as nucleic acid, the inventive transposase encoding sequence is preferably operably linked to a promoter. There are a variety of promoters that could be used including, but not limited to, constitutive promoters, tissue-specific promoters, inducible promoters, and the like. Promoters are regulatory signals that bind RNA polymerase in a cell to initiate transcription of a downstream (3' direction) coding sequence. A DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed and maintaining the correct reading frame to permit expression of the DNA sequence under the control of the expression control sequence to yield production of the desired protein product. One nucleic acid sequence encoding the inventive human mariner transposase protein is provided as SEQ ID NO:2. In addition to the conservative changes discussed above that would necessarily alter the transposase-encoding nucleic acid sequence (all of which are disclosed herein as well), there are other inventive DNA or RNA sequences encoding the inventive human mariner transposase protein. These inventive DNA or RNA sequences have the same amino acid sequence as an inventive human mariner transposase protein, but take advantage of the degeneracy of the three letter codons used to specify a particular amino acid. For example, it is well known in the art that various specific RNA codons (corresponding DNA codons, with a T substituted for a U) can be used interchangeably to code for specific amino acids.

Methods for manipulating DNA and proteins are known in the art and are explained in detail in the literature such as Sambrook et al, (1989) Molecular Cloning: A Laboratory Manual, Cold Spring Harbor Laboratory Press or Ausubel, R. M., ed. (1994). Current Protocols in Molecular Biology.

Another aspect of this invention refers to a transposon, also referred to herein as a transposable element, that includes a nucleic acid sequence (as defined above) positioned between at least two repeats (IRs and/or RSDs), at least one repeat on either side of the nucleic acid sequence. Preferably, the inventive transposon comprises a nucleic acid sequence positioned between at least two repeats (IRs and/or RSDs), wherein these repeats can bind to an inventive human mariner transposase protein as defined above and wherein the transposon is capable of inserting into DNA of a cell. In other words, repeats are defined as sequences which are recognized and bound by the inventive human mariner transposase as defined above.

The basic structure of an inventive transposon, which is bound by an inventive transposase, contains a pair of repeat sequences. Therein, the first repeat is typically located upstream to the above mentioned nucleic acid sequence and the second repeat is typically located downstream of this nucleic acid sequence. In this typical structure, the second repeat represents the same sequence as the first repeat, but shows an opposite reading direction as compared with the first repeat (5' and 3' ends of the complementary double strand sequences are exchanged). These repeats are then termed "inverted repeats" (IRs), due to the fact that both repeats are just inversely repeated sequences.

In a further constellation repeats as defined above may occur in a multiple number upstream and downstream of the above mentioned nucleic acid sequence. Then, preferably two, or eventually three, four, or more repeats are located upstream and/or downstream the above mentioned nucleic acid sequence. Preferably, the number of repeats located upstream and downstream of the above mentioned nucleic acid sequence is identical. If multiple copies of IRs exist on each terminus of the nucleic acid sequence, some of these multiple copies of the IRs at each terminus may have the same orientation as the IRs and are herein termed "repeats of the same direction" (RSD). In such a preferred situation the repeat assembly is termed IR/RSD.

For the (IR/RSD) structure, the multiple repeats located upstream and/or downstream of the above mentioned nucleic acid sequence may be arranged such as to be ligated directly to each other. Alternatively, these repeats may be separated by a spacer sequence. This spacer sequence is typically formed by a number of nucleic acids, preferably 50 to 200 nucleic acids.

In a preferred embodiment of the inventive transposon the at least two repeats (IRs and/or RSDs) are selected from sequences as shown in SEQ ID NOs: 4 and 5, or from a nucleic acid sequence showing at least 75%, preferably at least 80%, more preferably at least 85%, even more preferably at least 90%, and most preferably at least 95% or even 98% sequence identity with sequences as shown in SEQ ID NOs: 4 or 5.

The repeats (IRs and/or RSDs) as defined above preferably flank a nucleic acid sequence which is inserted into the DNA of a cell. The nucleic acid sequence can include all or part of an open reading frame of a gene (i.e., that part of a protein encoding gene), one or more expression control sequences (i.e., regulatory regions in nucleic acid) alone or together with all or part of an open reading frame. Preferred expression control sequences include, but are not limited to promoters, enhancers, border control elements, locus-control regions or silencers. In a preferred embodiment, the nucleic acid sequence comprises a promoter operably linked to at least a portion of an open reading frame. In a preferred embodiment, the inventive transposon comprises at least on of sequences according to SEQ ID NO 6 or 7. Finally the inventive transposons preferably occur as a linear transposon (extending from the 5' end to the 3' end, by convention) that can be used as a linear fragment or circularized, for example in a plasmid.

In one alternative embodiment of the inventive transposon, the nucleic acid sequence positioned between at least two repeats (IRs and/or RSDs) is a nucleic acid sequence as defined above and encodes an inventive human mariner transposase gene. In preferred embodiment, the inventive transposon comprises the sequence as shown by SEQ ID NO: 3 or a sequence or showing at least 75%, preferably at least 80%, more preferably at least 85%, even more preferably at least 90%, and most preferably at least 95% or even 98% sequence identity with the sequence as shown in SEQ ID NO: 3.

In another alternative embodiment of the inventive transposon, the nucleic acid sequence positioned between at least two repeats (IRs and/or RSDs) can be of any variety of recombinant proteins new or proteins known in the art. E.g. the protein encoded by the nucleic acid sequence can be a marker protein such as green fluorescent protein (GFP), the blue fluorescent protein (BFP), the photo activatable-GFP (PA-GFP), the yellow shifted green fluorescent protein (Yellow GFP), the yellow fluorescent protein (YFP), the enhanced yellow fluorescent protein (EYFP), the cyan fluorescent protein (CFP), the enhanced cyan fluorescent protein (ECFP), the monomeric red fluorescent protein (mRFP1), the kindling fluorescent protein (KFP1), aequorin, the autofluorescent proteins (AFPs), or the fluorescent proteins JRed, TurboGFP, PhiYFP and PhiYFP-m, tHc-Red (HcRed-Tandem), PS-CFP2 and KFP-Red (all available from EVRΩGEN, see also www.evrogen.com), or other suitable fluorescent proteins chloramphenicol acetyltransferase (CAT). The protein further may be selected from growth hormones, for example to promote growth in a transgenic animal, or from [beta]-galactosidase (lacZ), luciferase (LUC), and insulin-like growth factors (IGFs), α-anti-trypsin, erythropoietin (EPO), factors VIII and XI of the blood clotting system, LDL-receptor, GATA-1, etc. The nucleic acid sequence further may be a suicide gene encoding e.g. apoptotic or apoptose related enzymes and genes including AlF, Apaf e.g. Apaf-1, Apaf-2, Apaf-3, or APO-2 (L), APO-3 (L), Apopain, Bad, Bak, Bax, Bcl-2, Bcl-$x_L$, Bcl-$x_S$, bik, CAD, Calpain, Caspases e.g. Caspase-1, Caspase-2, Caspase-3, Caspase-4, Caspase-5, Caspase-6, Caspase-7, Caspase-8, Caspase-9, Caspase-10, Caspase-11, or Granzyme B, ced-3, ced-9, Ceramide, c-Jun, c-Myc, CPP32, crm A, Cytochrome c, D4-GDP-DI, Daxx, CdR1, DcR1, DD, DED, DISC, DNA-$PK_{CS}$, DR3, DR4, DR5, FADD/MORT-1, FAK, Fas, Fas-ligand CD95/fas (receptor), FLICE/MACH, FLIP, Fodrin, fos, G-Actin, Gas-2, Gelsolin, glucocorticoid/glucocorticoid receptor, granzyme A/B, hnRNPs C1/C2, ICAD, ICE, JNK, Lamin A/B, MAP, MCL-1, Mdm-2, MEKK-1, MORT-1, NEDD, NF-$_κ$B, NuMa, p53, PAK-2, PARP, Perforin, PITSLRE, PKCδ, pRb, Presenilin, prICE, RAIDD, Ras, RIP, Sphingomyelinase, SREBPs, thymidine kinase from Herpes simplex, TNF-α, TNF-α receptor, TRADD, TRAF2, TRAIL-R1, TRAIL-R2, TRAIL-R3, Transglutaminase, U1 70 kDa snRNP, YAMA, etc. Finally, the nucleic acid sequence may be selected from short RNA hairpin expression cassettes.

In a further preferred embodiment, the inventive transposon may occur in a so called "sandwich structure". In this "sandwich structure" the inventive transposon occurs in two copies flanking a (additional) gene of interest (being located between these two transposons). The gene flanked by the two transposons may directly be linked to the transposon(s). Alternatively, the active gene(s) may be separated by a spacer sequence from the transposon(s). This spacer sequence is typically formed by a number of nucleic acids, preferably 50 to 200 nucleic acids. Furthermore, the proteins or genes encoded by the two transposons, forming the sandwich structure, may be the same or different. When combining such a "sandwich structure" with an inventive transposase preferably the entire sequence starting from the first transposon until the end of the second transposon, will be inserted into a target (insertion) site of the inventive transposase.

Another embodiment of the present invention refers to a gene transfer system. As mentioned above, the inventive human mariner transposase protein preferably recognizes repeats (IRs and/or RSDs) on the inventive transposon. The gene transfer system of this invention, therefore, preferably comprises two components: the inventive transposase as defined above and a cloned, non-autonomous (i.e., non-self inserting) element or transposon (referred to herein as a transposon having at least two repeats (IRs and/or RSDs)) that carries the repeats (IRs and/or RSDs) of the transposon substrate DNA. When put together these two components provide active transposon activity and allow the transposon to be relocated. In use, the inventive transposase binds to the repeats (IRs and/or RSDs) and promotes insertion of the intervening nucleic acid sequence into DNA of a cell as defined below. More precisely, the inventive gene transfer system comprises an inventive transposon as defined above in combination with a human mariner transposase protein (or nucleic acid encoding the inventive human mariner transposase protein to provide its activity in a cell). Such an inventive combination preferably results in the insertion of the nucleic acid sequence into the DNA of the cell. Alternatively, it is possible to insert the transposon of the present invention into DNA of a cell through non-homologous recombination through a variety of reproducible mechanisms. In either event the inventive transposon can be used for gene transfer by using the inventive system.

The inventive gene transfer system mediates insertion of the inventive transposon into the DNA of a variety of cell types and a variety of species by using the inventive human mariner transposase protein. Preferably, such cells include any cell suitable in the present context, including but not limited to animal cells or cells from bacteria, fungi (e.g., yeast, etc.) or plants. Preferred animal cells can be vertebrate or invertebrate. Preferred invertebrate cells include cells derived from crustaceans or mollusks including, but not limited to shrimp, scallops, lobster, claims, or oysters. Preferred vertebrate cells include cells from fish, birds and other animals, e.g. cells from mammals including, but not limited to, rodents, such as rats or mice, ungulates, such as cows or goats, sheep, swine or cells from a human. In a specifically preferred embodiment, cells suitable for the present invention include CHO, HeLa and COS cells.

Furthermore, such cells, particularly cells derived from a mammals as defined above, can be pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). Such cells are advantageously used in order to affirm stable expression of the inventive transposase or to obtain a multiple number of cells already transfected with the components of the inventive gene transfer system. Additionally, cells such as oocytes, eggs, and one or more cells of an embryo may also be considered as targets for stable transfection with the present gene transfer system.

Cells receiving the inventive transposon and/or the inventive human mariner transposase protein and capable of inserting the inventive transposon into the DNA of that cell also include without being limited thereto, lymphocytes, hepatocytes, neural cells, muscle cells, a variety of blood cells, and a variety of cells of an organism, embryonic stem cells, somatic stem cells e.g. hematopoietic cells, embryos, zygotes, sperm cells (some of which are open to be manipulated by an in vitro setting).

In this context, the cell DNA that acts as a recipient of the transposon of this invention includes any DNA present in a cell (as mentioned above) to be transfected, if the inventive transposon is in contact with an inventive human mariner transposase protein within said cell. For example, the DNA can be part of the cell genome or it can be extrachromosomal, such as an episome, a plasmid, a circular or linear DNA fragment. Typical targets for insertion are e.g. double-stranded DNA.

The components of the inventive gene transfer system, i.e. the inventive human mariner transposase protein (either as a protein or encoded by an inventive nucleic acid) and the inventive transposon can be transfected into a cell, preferably into a cell as defined above, and more preferably into the same cell. Transfection of these components may furthermore occur in subsequent order or in parallel. E.g. the inventive human mariner transposase protein or its encoding nucleic acid may be transfected into a cell as defined above prior to, simultaneously with or subsequent to transfection of the inventive transposon. Alternatively, the inventive transposon may be transfected into a cell as defined above prior to, simultaneously with or subsequent to transfection of the inventive human mariner transposase protein or its encoding nucleic acid. If transfected parallel, preferably both components are provided in a separated formulation and/or mixed with each other directly prior to administration in order to avoid transposition prior to transfection. Additionally, administration of at least one component of the gene transfer system may occur repeatedly, e.g. by administering at least one, two or multiple doses of this component.

For any of the above transfection reactions, the inventive gene transfer system may be formulated in a suitable manner as known in the art, or as a pharmaceutical composition or kit as defined below.

Furthermore, the components of the inventive gene transfer system are preferably transfected into one or more cells by techniques such as particle bombardment, electroporation, microinjection, combining the components with lipid-containing vesicles, such as cationic lipid vesicles, DNA condensing reagents (e.g., calcium phosphate, polylysine or polyethyleneimine), and inserting the components (i.e. the nucleic acids thereof into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

As already mentioned above the nucleic acid encoding the inventive human mariner transposase protein may be RNA or DNA. Similarly, either the inventive nucleic acid encoding the inventive human mariner transposase protein or the transposon of this invention can be transfected into the cell as a linear fragment or as a circularized fragment, preferably as a plasmid or as recombinant viral DNA.

Furthermore, the inventive nucleic acid encoding the inventive human mariner transposase protein is thereby preferably stably or transiently inserted into the genome of the cell to facilitate temporary or prolonged expression of the inventive human mariner transposase protein in the cell.

The inventive gene transfer system as disclosed above represents a significant refinement of non-viral DNA-mediated gene transfer as discussed in the prior art. There are several reasons why the inventive non-viral gene transfer is superior to virus-mediated gene transfer for the development of new gene therapies. For example, adapting viruses as agents for gene therapy restricts genetic design to the constraints of that virus genome in terms of size, structure and regulation of expression. Non-viral vectors, like the genetic transfer systems of this invention, are generated largely from synthetic starting materials and are therefore more easily manufactured than viral vectors. Non-viral reagents are less likely to be immunogenic than viral agents making repeat administration possible. Non-viral vectors are more stable than viral vectors and therefore better suited for pharmaceutical formulation and application than are viral vectors. Additionally, the inventive gene transfer system is a non-viral gene transfer system that facilitates insertion into DNA and markedly improves the frequency of stable gene transfer.

The inventive transposon furthermore allows easy handling in vivo as well as in vitro due to efficient transcription/translation across the short IRs, comprising about 30 bp. Furthermore, such an improved transcription/translation across the IRs also enhances reliability and effectiveness of gene transfer methods and therapies as well as of experimental results based on use of the inventive transposons.

The present invention furthermore provides an efficient method for producing transgenic animals, including the step of applying the inventive gene transfer system to an animal. Prior to this invention, transgenic DNA has not been efficiently inserted into chromosomes. Only about one in a million of the foreign DNA molecules is inserted into the cellular genome, generally several cleavage cycles into development. Consequently, most transgenic animals are mosaic (Hackett et al. (1993). The molecular biology of transgenic fish. In Biochemistry and Molecular Biology of Fishes (Hochachka & Mommsen, eds) Vol. 2, pp. 207-240). As a result, animals raised from embryos into which transgenic DNA has been delivered must be cultured until gametes can be assayed for the presence of inserted foreign DNA. Many transgenic animals fail to express the transgene due to position effects. A simple, reliable procedure that directs early insertion of exogenous DNA into the chromosomes of animals at the one-cell stage is needed. The present system helps to fill this need.

More particularly, the gene transfer system of this invention can readily be used to produce transgenic animals that carry a particular marker or express a particular protein in one or more cells of the animal. Generally, methods for producing transgenic animals are known in the art and incorporation of the inventive gene transfer system into these techniques does not require undue experimentation. E.g. there are a variety of methods for producing transgenic animals for research or for protein production including, but not limited to Hackett et al. (1993, supra). Other methods for producing transgenic animals include the teachings of M. Markkula et al. (Rev.

Reprod., 1, 97-106 (1996); R. T. Wall et al., J. Dairy Sci., 80, 2213-2224 (1997)), J. C. Dalton, et al. (Adv. Exp. Med. Biol., 411, 419-428 (1997)) and H. Lubon et al. (Transfus. Med. Rev., 10, 131-143 (1996)). The inventive gene transfer system has also been tested through the introduction of the inventive nucleic acid with a marker protein into HeLa and CHO-K1 cells. Furthermore, there are two methods to achieve improved stocks of commercially important transgenic animals. The first is classical breeding, which has worked well for land animals, but it takes decades to make major changes. A review by Hackett et al. (1997) points out that by controlled breeding, growth rates in coho salmon (*Oncorhynchus kisutch*) increased 60% over four generations and body weights of two strains of channel catfish (*Ictalurus punctatus*) were increased 21 to 29% over three generations. The second method is genetic engineering, a selective process by which genes are inserted into the chromosomes of animals or plants to give these organisms a new trait or characteristic, like improved growth or greater resistance to disease.

Also encompassed by the inventive methods for preparing transgenic animals are e.g. methods for creating transgenic fish by microinjecting the gene transfer system into a cell of an embryo of the fish or a method for introducing the gene transfer system into mouse embryonic stem cells. Methods for producing transgenic mice from embryonic stem cells are well known in the art. E.g. a review of the production of biopharmaceutical proteins in the milk of transgenic dairy animals (see Young et al., BIO PHARM (1997), 10, 34-38) and the references provided therein detail methods and strategies for producing recombinant proteins in milk. The methods and the gene transfer system of this invention can be readily incorporated into these transgenic techniques without undue experimentation in view of what is known in the art and particularly in view of this disclosure.

Another embodiment of the present invention refers to a transgenic animal produced by such methods as disclosed above, preferably by using the inventive gene transfer system. Inventive transgenic animals preferably contain a nucleic acid sequence inserted into the genome of the animal by the inventive gene transfer system, thereby enabling the transgenic animal to produce its gene product, e.g. a protein. In inventive transgenic animals this protein is preferably a product for isolation from a cell. Therefore, in one alternative, inventive transgenic animals may be used as bioreactors. The inventive protein can be produced in quantity in milk, urine, blood or eggs. Promoters can be used that promote expression in milk, urine, blood or eggs and these promoters include, but are not limited to, casein promoter, the mouse urinary protein promoter, [beta]-globin promoter and the ovalbumin promoter respectively. Recombinant growth hormone, recombinant insulin, and a variety of other recombinant proteins have been produced using other methods for producing protein in a cell. Nucleic acids encoding these or other proteins can be inserted into the transposon of this invention and transfected into a cell. Efficient transfection of the inventive transposon as defined above into the DNA of a cell occurs when an inventive human mariner transposase protein is present. Where the cell is part of a tissue or part of a transgenic animal, large amounts of recombinant protein can be obtained.

Inventive transgenic animals may be selected from vertebrates and invertebrates, selected form e.g. fish, birds, mammals including, but not limited to, rodents, such as rats or mice, ungulates, such as cows or goats, sheep, swine or humans.

The present invention furthermore provides a method for gene therapy comprising the step of introducing the inventive gene transfer system into cells as defined above. Therefore, the inventive transposon as defined above preferably comprises a gene to provide a gene therapy to a cell or an organism. Preferably, the gene is placed under the control of a tissue specific promoter or of a ubiquitous promoter or one or more other expression control regions for the expression of a gene in a cell in need of that gene. A variety of genes are being tested for a variety of gene therapies including, but not limited to, the CFTR gene for cystic fibrosis, adenosine deaminase (ADA) for immune system disorders, factor IX and interleukin-2 (IL-2) for blood cell diseases, alpha-1-antitrypsin for lung disease, and tumor necrosis factors (INFs) and multiple drug resistance (MDR) proteins for cancer therapies. These and a variety of human or animal specific gene sequences including gene sequences to encode marker proteins and a variety of recombinant proteins are available in the known gene databases such as GenBank, and the like.

An advantage of the inventive gene transfer system particular for gene therapy purposes is that it is not limited to a great extent by the size of the intervening nucleic acid sequence positioned between the repeats (IRs and/or RSDs). The inventive human mariner transposase protein may preferably be used to insert inventive transposons ranging from 1.3 kilobases (kb) to about 5.0 kb. Furthermore, the mariner transposase preferably mobilizes transposons up to about 13 kb. There is no known limit on the size of the nucleic acid sequence that can be inserted into DNA of a cell using the inventive human mariner transposase protein.

Particularly for gene therapy purposes, but also for other inventive purposes the inventive gene transfer system may be transfected into cells by a variety of methods, e.g. by microinjection, lipid-mediated strategies or by viral-mediated strategies. For example, where microinjection is used, there is very little restraint on the size of the intervening sequence of the transposon of this invention. Similarly, lipid-mediated strategies do not have substantial size limitations. However, other strategies for introducing the gene transfer system into a cell, such as viral-mediated strategies could limit the length of the nucleic acid sequence positioned between the repeats (IRs and/or RSDs), according to this invention.

In this context, the inventive gene transfer system as defined above can be delivered to cells via viruses, including retroviruses (such as lentiviruses, etc.), adenoviruses, adeno-associated viruses, herpes viruses, and others. There are several potential combinations of delivery mechanisms for the inventive transposon portion containing the transgene of interest flanked by the terminal repeats (IRs and/or RSDs) and the gene encoding the inventive transposase. For example, both the inventive transposon and the inventive transposase gene can be contained together on the same recombinant viral genome; a single infection delivers both parts of the inventive gene transfer system such that expression of the transposase then directs cleavage of the transposon from the recombinant viral genome for subsequent insertion into a cellular chromosome. In another example, the inventive transposase and the inventive transposon can be delivered separately by a combination of viruses and/or non-viral systems such as lipid-containing reagents. In these cases either the transposon and/or the transposase gene can be delivered by a recombinant virus. In every case, the expressed transposase gene directs liberation of the transposon from its carrier DNA (viral genome) for insertion into chromosomal DNA.

In a specific embodiment of the present invention inventive transposons may be utilized for insertional mutagenesis, preferably followed by identification of the mutated gene. DNA transposons, particularly the inventive transposons, have several advantages compared to approaches in the prior art, e.g. with respect to viral and retroviral methods. For example, unlike proviral insertions, transposon insertions can be remobilized by supplying the transposase activity in trans. Thus, instead of performing time-consuming microinjections, it is possible according to the present invention to generate transposon insertions at new loci by crossing stocks transgenic for the above mentioned two components of the transposon system, the inventive transposon and the inventive transposase. In a preferred embodiment the inventive gene transfer system is directed to the germline of the experimental animals in order to mutagenize germ cells. Alternatively, transposase expression can be directed to particular tissues or organs by using a variety of specific promoters. In addition, remobilization of a mutagenic transposon out of its insertion site can be used to isolate revertants and, if transposon excision is associated with a deletion of flanking DNA, the inventive gene transfer system may be used to generate deletion mutations. Furthermore, since transposons are composed of DNA, and can be maintained in simple plasmids, inventive transposons and particularly the use of the inventive gene transfer system is much safer and easier to work with than highly infectious retroviruses. The transposase activity can be supplied in the form of DNA, mRNA or protein as defined above in the desired experimental phase.

When the inventive gene transfer system is used in insertional mutagenesis screens, inventive transposons preferably comprise four major classes of constructs to identify the mutated genes rapidly (see FIG. 10), i.e. enhancer traps, promoter traps, polyA traps and gene traps (or exon traps) as defined below. These inventive transposons preferably contain a reporter gene, which should be expressed depending on the genetic context of the integration.

In inventive enhancer traps (see FIG. 10a), the expression of the reporter typically requires the presence of a genomic cis-regulator to act on an attenuated promoter within the integrated construct.

Inventive promoter traps (see FIG. 10 b) typically contain no promoter at all. In order to ensure expression of vectors, the vectors are preferably in-frame in an exon or close downstream to a promoter of an expressed gene.

In inventive polyA traps (see FIG. 10c), the marker gene preferably lacks a polyA signal, but contains a splice donor (SD) site. Thus, when integrating into an intron, a fusion transcript can be synthesized comprising the marker and the downstream exons of the trapped gene.

Inventive gene traps (or exon traps) (see FIG. 10d) typically lack promoters, but are equipped with a splice acceptor (SA) preceding the marker gene. Reporter activation occurs if the vector is integrated into an expressed gene, and splicing between the reporter and an upstream exon takes place.

Finally, inventive gene trap and polyA trap cassettes can be combined. In that case, the marker of the polyA trap part preferably carries a promoter so that the vector can also trap downstream exons, and both upstream and downstream fusion transcripts of the trapped gene can be obtained. These inventive constructs also offer the possibility to visualize spatial and temporal expression patterns of the mutated genes by using LacZ or fluorescent proteins as a marker gene.

In a specific form of the inventive method, the present invention furthermore provides an efficient system for gene tagging by introducing a "tag" into a genomic sequence using the inventive gene transfer system. Any of the above mentioned inventive transposons, e.g. enhancer traps, promoter traps, polyA traps and gene traps (or exon traps), etc. may be used.

Due to their inherent ability to move from one chromosomal location to another within and between genomes, inventive transposons are suitable as genetic vectors for genetic manipulations in several organisms. Generally, transposon tagging is a technique in which transposons are mobilized to "hop" into genes, thereby inactivating them by insertional mutagenesis. These methods are discussed e.g. by Evans et al., TIG 1997 13, 370-374. In the inventive process, the inactivated genes are "tagged" by the transposon which then can be used to recover the mutated allele. The ability of the human and other genome projects to acquire gene sequence data has outpaced the ability of scientists to ascribe biological function to the new genes. Therefore, the present invention provides an efficient method for introducing a tag into the genome of a cell. Where the tag is inserted into a location in the cell that disrupts expression of a protein that is associated with a particular phenotype, expression of an altered phenotype in a cell containing the nucleic acid of this invention permits the association of a particular phenotype with a particular gene that has been disrupted by the transposon of this invention. Preferably, the inventive transposon as defined above functions as a tag. Primers designed to sequence the genomic DNA flanking the transposon of this invention can be used to obtain sequence information about the disrupted gene.

In a further embodiment the present invention also provides an efficient system for gene discovery, e.g. genome mapping, by introducing an inventive transposon as defined above into a gene using the inventive gene transfer system. In one example, the inventive transposon in combination with the inventive human mariner transposase protein or a nucleic acid encoding the inventive human mariner transposase protein is transfected into a cell. The transposon preferably comprises a nucleic acid sequence positioned between at least two repeats (IRs and/or RSDs), wherein the repeats (IRs and/or RSDs) bind to the inventive human mariner transposase protein and wherein the transposon is inserted into the DNA of the cell in the presence of the inventive human mariner transposase protein. In a preferred embodiment, the nucleic acid sequence includes a marker protein, such as GFP and a restriction endonuclease recognition site, preferably a 6-base recognition sequence. Following insertion, the cell DNA is isolated and digested with the restriction endonuclease. Where a restriction endonuclease is used that employs a 6-base recognition sequence, the cell DNA is cut into about 4000-bp fragments on average. These fragments can be either cloned or linkers can be added to the ends of the digested fragments to provide complementary sequence for PCR primers. Where linkers are added, PCR reactions are used to amplify fragments using primers from the linkers and primers binding to the direct repeats of the repeats (IRs and/or RSDs) in the transposon. The amplified fragments are then sequenced and the DNA flanking the direct repeats is used to search computer databases such as GenBank.

Using the inventive gene transfer system for methods as disclosed above such as gene discovery and/or gene tagging, permits e.g. the following:

1) identification, isolation, and characterization of genes involved with growth and development through the use of transposons as insertional mutagens (e.g., see Kaiser et al., 1995, "Eukaryotic transposons as tools to study gene structure and function." In Mobile Genetic Elements, IRL Press, pp. 69-100).

2) identification, isolation and characterization of transcriptional regulatory sequences controlling growth and development.

3) use of marker constructs for quantitative trait loci (QTL) analysis.

4) identification of genetic loci of economically important traits, besides those for growth and development, i.e., disease resistance (e.g., Anderson et al., 1996, Mol. Mar. Biol. Biotech., 5, 105-113). In one example, the system of this invention can be used to produce sterile transgenic fish. Broodstock with inactivated genes could be mated to produce sterile offspring for either biological containment or for maximizing growth rates in aquacultured fish.

The inventive gene transfer system can also be used as part of a method for working with or for screening a library of recombinant sequences, for example, to assess the function of the sequences or to screen for protein expression, or to assess the effect of a particular protein or a particular expression control region on a particular cell type. In this example, a library of recombinant sequences, such as the product of a combinatorial library or the product of gene shuffling, both techniques now known in the art and not the focus of this invention, can be inserted into the transposon of this invention to produce a library of transposons with varying nucleic acid sequences positioned between constant repeat sequences (IRs and/or RSDs). The library is then transfected into cells together with the inventive human mariner transposase protein as discussed above.

In another embodiment of this invention, the invention provides a method for mobilizing a nucleic acid sequence in a cell. According to this method the inventive transposon is inserted into DNA of a cell, as disclosed above. Additionally, human mariner transposase protein or nucleic acid encoding the inventive human mariner transposase protein is transfected into the cell and the protein is able to mobilize (i.e. move) the transposon from a first position within the DNA of the cell to a second position within the DNA of the cell. The DNA of the cell is preferably genomic DNA or extrachromosomal DNA. The inventive method allows movement of the transposon from one location in the genome to another location in the genome, or for example, from a plasmid in a cell to the genome of that cell.

Additionally, the inventive gene transfer system can also be used as part of a method involving RNA-interference techniques. RNA interference (RNAi), is a technique in which exogenous, double-stranded RNAs (dsRNAs), being complementary to mRNA's or genes/gene fragments of the cell, are introduced into this cell to specifically bind to a particular mRNA and/or a gene and thereby diminishing or abolishing gene expression. The technique has proven effective in *Drosophila, Caenorhabditis elegans*, plants, and recently, in mammalian cell cultures. In order to apply this technique in context with the present invention, the inventive transposon preferably contains short hairpin expression cassettes encoding small interfering RNAs (siRNAs), which are complementary to mRNA's and/or genes/gene fragments of the cell. These siRNAs have preferably a length of 20 to 30 nucleic acids, more preferably a length of 20 to 25 nucleic acids and most preferably a length of 21 to 23 nucleic acids. The siRNA may be directed to any mRNA and/or a gene, that encodes any protein as defined above, e.g. an oncogene. This inventive use, particularly the use of inventive transposons for integration of siRNA vectors into the host genome advantageously provides a long-term expression of siRNA in vitro or in vivo and thus enables a long-term silencing of specific gene products.

The present invention further refers to pharmaceutical compositions containing either
    an inventive human transposase as a protein or encoded by an inventive nucleic acid, and/or
    an inventive transposon; or
    an inventive gene transfer system as defined above comprising an inventive human transposase as a protein or encoded by an inventive nucleic acid, in combination with an inventive transposon.

The pharmaceutical composition may optionally be provided together with a pharmaceutically acceptable carrier, adjuvant or vehicle. In this context, a pharmaceutically acceptable carrier, adjuvant, or vehicle according to the invention refers to a non-toxic carrier, adjuvant or vehicle that does not destroy the pharmacological activity of the component(s) with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, topically, rectally, nasally, buccally, vaginally or via an implanted reservoir.

The term parenteral as used herein includes subcutaneous, intravenous, intramuscular, intra-articular, intra-synovial, intrasternal, intrathecal, intrahepatic, intralesional and intracranial injection or infusion techniques. Preferably, the pharmaceutical compositions are administered orally, intraperitoneally or intravenously. Sterile injectable forms of the pharmaceutical compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch.

When aqueous suspensions are required for oral use, the active ingredient is combined with emulsifying and suspending agents. If desired, certain sweetening, flavouring or colouring agents may also be added.

Alternatively, the pharmaceutically acceptable compositions of this invention may be administered in the form of suppositories for rectal administration. These can be prepared by mixing the inventive gene transfer system or components thereof with a suitable non-irritating excipient that is solid at room temperature but liquid at rectal temperature and Therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the inventive gene transfer system or components thereof suspended or dissolved in one or more carriers. Carriers for topical administration of the components of this invention include, but are not limited to, mineral oil, liquid petrolatum, white petrolatum, propylene glycol, polyoxyethylene, polyoxypropylene component, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the components of the present invention that may be combined with the carrier materials to produce a composition in a single dosage form will vary depending upon the host treated, the particular mode of administration. It has to be noted that a specific dosage and treatment regimen for any particular patient will depend upon a variety of factors, including the activity of the specific component employed, the age, body weight, general health, sex, diet, time of administration, rate of excretion, drug combination, and the judgment of the treating physician and the severity of the particular disease being treated. The amount of a component of the present invention in the composition will also depend upon the particular component(s) in the composition.

The inventive pharmaceutical composition is preferably suitable for the treatment of diseases, particular diseases caused by gene defects such as cystic fibrosis, hypercholesterolemia, hemophilia, immune deficiencies including HIV, Huntington disease, α-anti-Trypsin deficiency, as well as cancer selected from colon cancer, melanomas, kidney cancer, lymphoma, acute myeloid leukemia (AML), acute lymphoid leukemia (ALL), chronic myeloid leukemia (CML), chronic lymphocytic leukemia (CLL), gastrointestinal tumors, lung cancer, gliomas, thyroid cancer, mamma carcinomas, prostate tumors, hepatomas, diverse virus-induced tumors such as e.g. papilloma virus induced carcinomas (e.g. cervix carcinoma), adeno carcinomas, herpes virus induced tumors (e.g. Burkitt's lymphoma, EBV induced B cell lymphoma), Hepatitis B induced tumors (Hepato cell carcinomas), HTLV-1 und HTLV-2 induced lymphoma, akustikus neurinoma, lungen cancer, pharyngeal cancer, anal carcinoma, glioblastoma, lymphoma, rectum carcinoma, astrocytoma, brain tumors, stomach cancer, retinoblastoma, basalioma, brain metastases, medullo blastoma, vaginal cancer, pancreatic cancer, testis cancer, melanoma, bladder cancer, Hodgkin syndrome, meningeoma, Schneeberger's disease, bronchial carcinoma, pituitary cancer, mycosis fungoides, gullet cancer, breast cancer, neurinoma, spinalioma, Burkitt's lymphoma, lyryngeal cancer, thymoma, corpus carcinoma, bone cancer, non-Hodgkin lymphoma, urethra cancer, CUP-syndrome, oligodendroglioma, vulva cancer, intestinal cancer, oesphagus carcinoma, small intestine tumors, craniopharyngeoma, ovarial carcinoma, ovarian cancer, liver cancer, leukemia, or cancers of the skin or the eye; etc.

The present invention finally refers to kits comprising:
- an inventive human mariner transposase as a protein or encoded by an inventive nucleic acid, and/or
- an inventive transposon; or
- an inventive gene transfer system as defined above comprising an inventive human transposase as a protein or encoded by an inventive nucleic acid, in combination with an inventive transposon;

optionally together with a pharmaceutically acceptable carrier, adjuvant or vehicle, and optional with instructions for use.

Any of the components of the inventive kit may be administered and/or transfected into cells in a subsequent order or in parallel. E.g. the inventive human mariner transposase protein or its encoding nucleic acid may be administered and/or transfected into a cell as defined above prior to, simultaneously with or subsequent to administration and/or transfection of the inventive transposon. Alternatively, the inventive transposon may be transfected into a cell as defined above prior to, simultaneously with or subsequent to transfection of the inventive human mariner transposase protein or its encoding nucleic acid. If transfected parallel, preferably both components are provided in a separated formulation and/or mixed with each other directly prior to administration in order to avoid transposition prior to transfection. Additionally, administration and/or transfection of at least one component of the inventive kit may occur in a time staggered mode, e.g. by administering multiple doses of this component.

All references, patents and publications cited herein are expressly incorporated by reference into this disclosure. Particular embodiments of this invention will be discussed in detail and reference has been made to possible variations within the scope of this invention. There are a variety of alternative techniques and procedures available to those of

DESCRIPTION OF FIGURES

As shown in FIG. 1, the transposase initiates the excision of the transposon with staggered cuts and inserts it at a TA target nucleotide (insertion site). The single-stranded gaps at the insertion site as well as the excision of the double-strand DNA breaks in the donor DNA are repaired by the host DNA repair machinery. After repair, the target TA is duplicated at the insertion site, and a small footprint is left behind at the place of excision.

FIG. 2: Alignment of the conceptual amino acid sequence translation of the human Hsmar1 consensus transposase gene (SEQ ID NO:1) and clone No. 1 Hsmar1 transposase coding region, identified from the chimpanzee genome. The aspartate residues of the DDD triad is marked with §.

FIG. 3: Alignment of the predicted amino acid sequences of the cecropia subfamily of mariner transposases. The presumptive NLSs are underlined, the DDD triad is marked with §. Asterisks mark those positions where the Hsmar1 sequence differs from the conserved transposase sequences and where PCR mutagenesis was used to obtain the conserved amino acids. (SEQ ID NO:1)

FIG. 4: Alignment of amino acid sequences covering the predicted non-specific DNA binding domain and the N terminal part of the catalytic domain of phylogenetically distant mariner transposases. The Hsmar1 sequence is underlined, the first D of the DDD triad is marked with an §. The alignment reveals the almost complete conservation of leucine at position 139 (asterisks), which implies that this amino acid is indispensable for mariner transposase activity. (SEQ ID NOs: 25-51)

FIG. 6: Sequence of the Hsmar1-Prime transposon. The IRs are shown with a black background as a consecutive number of amino acids. The encoded amino acids of the transposase are indicated under the nucleotide sequence. (SEQ ID NO:2) The presumptive nuclear localization signal is underlined. Asterisks show positions, where nucleotides were replaced to gain the majority-rule Hsmar1 consensus sequence. Single amino acids with a black background indicate modified positions deduced by comparative sequence alignment analysis of cecrophia-type transposases.

FIG. 7 shows results of transposition experiments with Hsmar1-cons, Hsmar1-Prime. Particularly,
(A) shows a table of mutant Hsmar1 transposase genes generated during the course of mutagenesis. None, but the Hsmar1-Prime transposase showed activity in transposition assays
(B) shows the numbers of G418 resistant colonies (y-axis) after cotransfection experiments of different helper plasmids with the pHsmar1-neo donor transposon (x-axis). Cotransfection of pFV-FP served as control. Numbers of G418 resistant colonies are indicated on the y-axis.

FIG. 8: Cut and paste transposition of Hsmar1-Prime. FIG. 8 shows results of transposition experiments with Hsmar1-cons, Hsmar7-Prime. Particularly, (A) shows an agarose gel with PCR products obtained by the excision assay after transfection of different helper and donor plasmids—indicated in the table below—into CHO-K1 cells. The 260 bp long band is indicative of the excision of the Hsmar1 element and the subsequent repair of donor plasmid (B) shows an sequence analysis of excision sites. Above, sequences of the transposon-plasmid backbone junction are shown in italics. Below, sequenced PCR products are listed; the flanking TA dinucleotides are depicted in bold letters, the transposon footprint is underlined. (C) shows the flanking sequences of de novo Hsmar1 transposon insertions in the human genome. The target TA dinucleotides (bold) were duplicated after transposon insertion. Chromosomes hit by the insertions are listed to the right, i.e. chromosomes 10, 7 and 1. (SEQ ID NOs:1-24)

FIG. 9 shows results of Excision experiments of the autonomous Hsmar1 in Chinese hamster cells. Therefore CHO-K1 cells were transfected with different Hsmar1 plasmids as indicated in the table and the extracted plasmid DNA was subjected to PCR analysis to detect excision of the Hsmar1 elements. The appearance of the 260 bp long diagnostic band in lane 2 reveals that the complete Hsmar1 element can autonomously catalyze its excision from the vector plasmid.

FIG. 10: Transposon-based gene trapping vectors. FIG. 10 shows a schematic overview of inventive transposon-based gene trapping vectors. On top, a hypothetical transcription unit is depicted with an upstream regulatory element (cross), a promoter (arrow with triangular ending), three exons (boxes) and a polyadenylation signal (pA). Major classes of transposon-based trapping constructs and spliced transcripts are shown below (a=enhancer traps, b=promoter traps, c=polyA traps and d=gene traps). Transposon inverted repeats are indicated by arrows with blunt ends, different promoters are indicated, SD and SA represent splice donor and slice acceptor sites, respectively.

EXAMPLES

1. Molecular Reconstruction of Hsmar1

Figure 1:
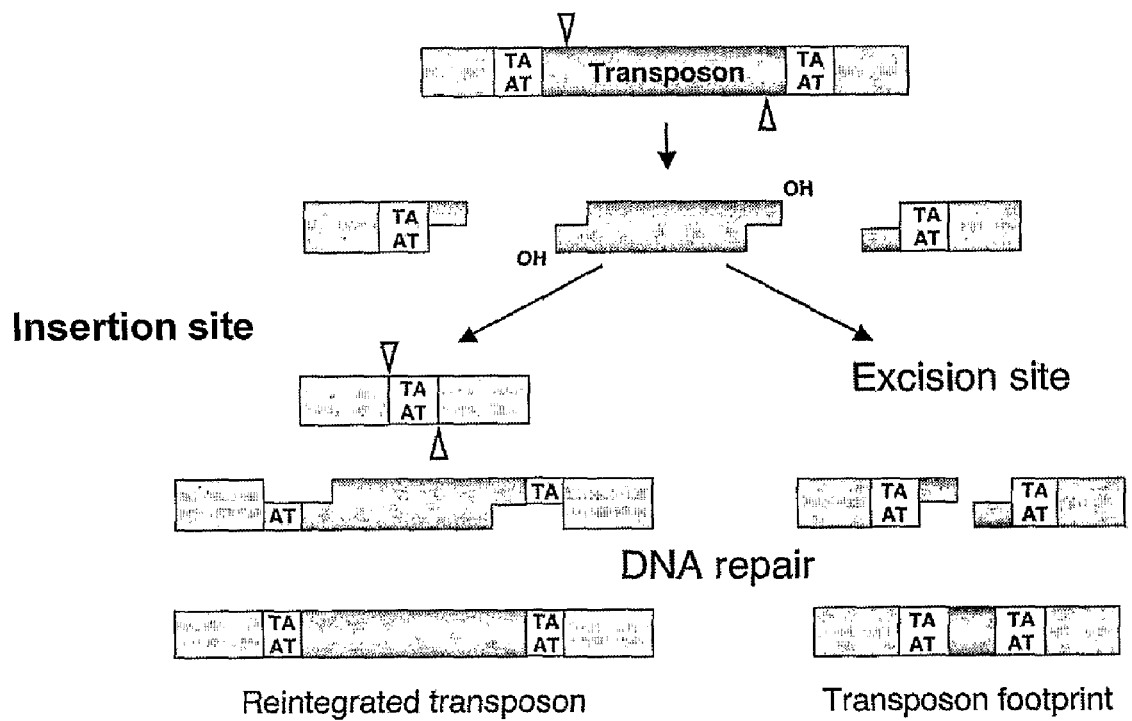
FIG. 1: Structure and mechanism of cut and paste mechanism of transposition.
Figure 5:
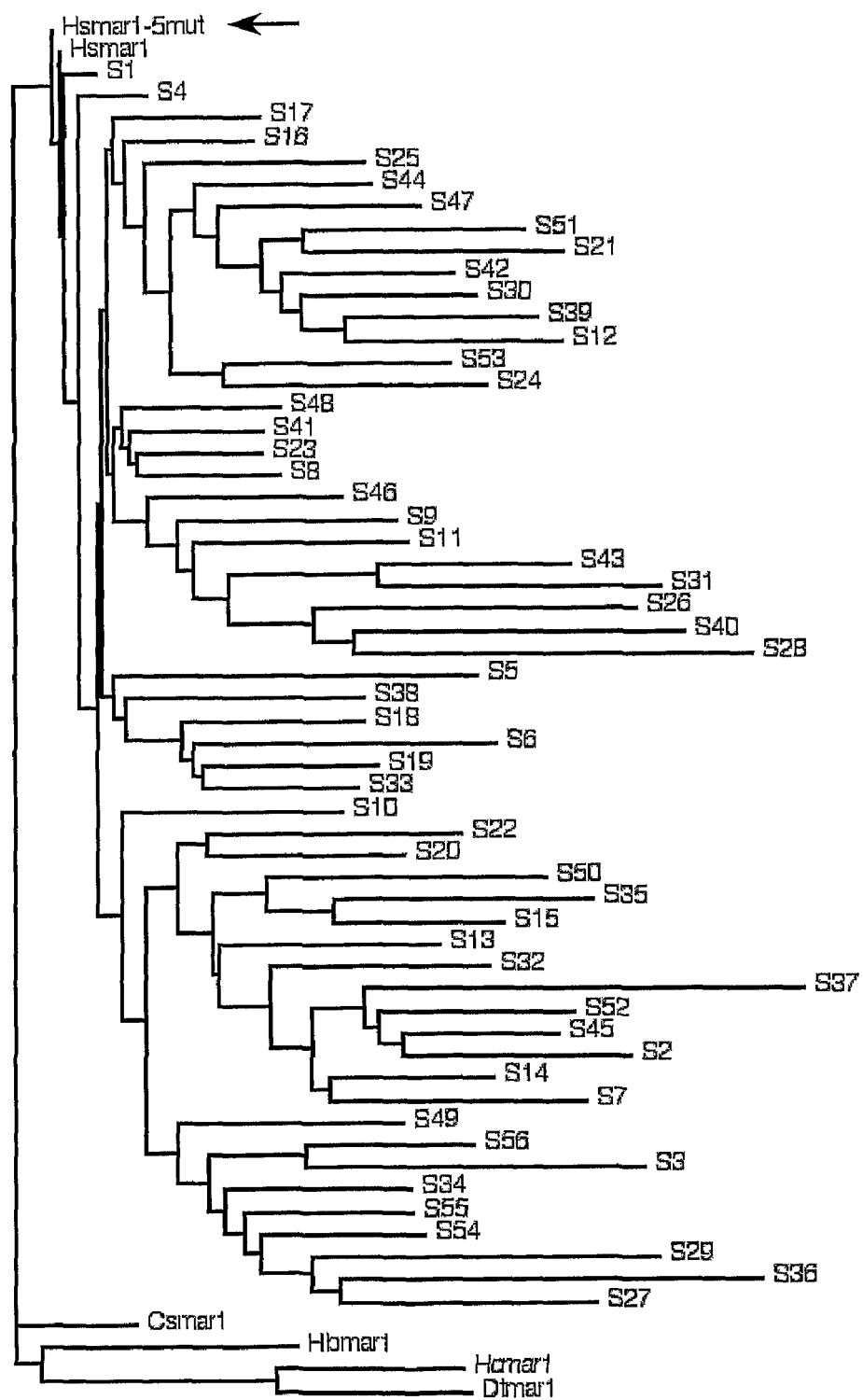
FIG. 5: Phylogenetic analysis of the mutated Hsmar1 transposase sequence. Shown is a phylogenetic analysis obtained by aligning conceptual amino acid sequences of 56 human BLAST-hits (S) and those of cecropia mariner elements along with a consensus sequence for the human mariner Hsmar1 and the mutated transposase sequence [(Hsmar1-5mut), arrow] by using T-Coffee default settings (Notredame et al., 2000). The maximum likelihood tree was rooted on the cecropia subfamily of transposases and displayed with TreeView.

Since only about 1% of the human genome sequences was available at the time when the Hsmar1 consensus sequence was generated, we searched the complete human sequence database with the putative consensus Hsmar1 transposase coding sequences using BLASTN. Alignment of the conceptually translated amino acid sequences of the 35 most similar hits did not predict novel amino acids in the Hsmar1 transposase sequence (data not shown). Therefore we assumed that the Hsmar1 transposase sequence by Robertson and Zumpano (1997, supra) indeed reflects an inactive form of the archaic transposon from which the present human genomic copies derived, and we aimed to reconstruct the active transposase and its coding sequence. Studies of Hsmar1 genomic copies and cDNA sequences of the human genome showed that they differ from their consensus by an average of 7.8% in DNA sequence and 7.5 indels per kilobase pairs. Any Hsmar1 transposase coding region more similar to the putative consensus sequence could ease the reconstruction procedure. The search for transposase gene versions in phylogenetically related genomes significantly shortened the reconstruction of Frog Prince transposase gene. Hence, the ancient Hsmar1 sequences entered the human genome lineage in an early phase of primate evolution, Hsmar1 copies are represented in other hominids too (Robertson and Zumpano, 1997, supra). Thus, the open reading frame trapping method was used to search for uninterrupted ORFs in the chimpanzee genome. Hsmar1 transposase coding sequences were PCR amplified from chimpanzee genomic DNA samples isolated from COS cells. Among the identified transposase ORFs No. 1 had the most similar sequence to that of the consensus gene and showed 5.3% DNA sequence divergence, and 6.1% alteration on the amino acid level (FIG. 1). The alignment of the conceptual amino acid sequence translation of the human Hsmar1 consensus transposase gene and clone No. 1 Hsmar1 transposase coding region, identified from the chimpanzee genome is shown in FIG. 3. The aspartate residues of the DDD triad are marked with "§".

This coding region was subjected to a series of site-specific PCR mutagenesis to correct 21 missense codons of the chimpanzee ORF and to derive the consensus transposase gene. Next, the consensus 5' and 3' non-coding transposon sequences including the 30 bp long terminal IRs were assembled from oligonucleotides. The IR sequences and the consensus transposase gene were separated to the transposon donor plasmid containing an SV40 promoter driven neo cassette flanked by the Hsmar1 IRs (pHsmar-neo), and the helper plasmid (pFV-Hsmar1-cons) expressing the Hsmar1 transposase gene, respectively.

When the donor and helper plasmids were transfected into cultured HeLa or CHO-K1 cells, no transposition activity was measured with the standard excision-, or transposition assays. These data suggested that the majority-rule consensus Hsmar1 sequence does not represent a functional transposase gene. Thus, it seemed that in the human genome already inactive Hsmar1 elements were mobilized in trans and increased in copy number to such an extent that by now these defective elements represent the majority; consequently, their majority-rule consensus sequence does not reflect that of the archetypical transposase gene.

Since it was unlikely that the same mutations are fixed during vertical inactivation in different organisms, a way of addressing the above problem was to compare the transposase coding regions of those mariner elements phylogenetically related to Hsmar1. Hsmar1 is a member of the cecropia subfamily of mariners (Lampe, D. J., Walden, K. K. & Robertson, H. M. (2001). Loss of transposase-DNA interaction may underlie the divergence of mariner family transposons and the ability of more than one mariner to occupy the same genome. Mol Biol Evol 18, 954-61), which includes the Hbmar1 from the parasite nematode *Heterorhabditis bacteriophora*, (Grenier, E., Abadon, M., Brunet, F., Capy, P. & Abad, P. (1999). A mariner-like transposon in the insect parasite nematode *Heterorhabditis bacteriophora*. J Mol Evol 48, 328-36), Hcmar1 from the cecropia moth *Hyalophora cecropia*, (Lidholm, D. A., Gudmundsson, G. H. & Boman, H. G. (1991). A highly repetitive, mariner-like element in the genome of *Hyalophora cecropia*. J Biol Chem 266, 11518-21), Dtmar1 from the planarian worm *Dugesia tigrina* (Garcia-Fernandez, J., Bayascas-Ramirez, J. R., Marfany, G., Munoz-Marmol, A. M., Casali, A., Baguna, J. & Salo, E. (1995). High copy number of highly similar mariner-like transposons in planarian (Platyhelminthe): evidence for a trans-phyla horizontal transfer. Mol Biol Evol 12, 421-31), and Cmar1 from a coleopteran beetle species (Robertson, H. M. & MacLeod, E. G. (1993). Five major subfamilies of mariner transposons in insects, including the Mediterranean fruit fly, and related arthropods. Insect Mol Biol 2, 125-39). In spite of the enormous phylogenetic distances between the different worm, insect and primate host genome lineages these transposases show up to approximately 80% similarity with each other at the amino acid level. After aligning the amino acid sequences of the above transposases, we found four amino acid positions where the consensus Hsmar1 transposase diverged from the completely conserved sequence of the cecropia-type transposases (FIG. 3).

Presuming that these amino acids are conserved within the subfamily because they are required for transposase activity, these positions were subjected to a second set of PCR mutagenesis.

Among the substitutions, R53C is within the presumptive bipartial nuclear localization signal of the transposase (Auge-Gouillou, C., Bigot, Y., Pollet, N., Hamelin, M. H., Meunier-Rotival, M. & Periquet, G. (1995). Human and other mammalian genomes contain transposons of the mariner family. FEBS Lett 368, 541-6). At this position the predominant triplet of the human and chimpanzee genomic copies is TGC, encoding cystein (C), however we found a remarkable number of CAC triplet too within genomic Hsmar1 copies in this position (data not shown). There are two reasons to assume that in the ancestrally active sequence this triplet was CGC, encoding arginine (R). First, CpG dinucleotides of other ancient transposons of the human genome have been ascribed to be hypermutable due to the methylation and subsequent deamination of C, resulting in T (Britten, R. J., Baron, W. F., Stout, D. B. & Davidson, E. H. (1988). Sources and evolution of human Alu repeated sequences. Proc Natl Acad Sci USA 85, 4770-4). Such conversion leads to CA nucleotides in the other DNA strand. Second, the assumed original CGC triplet encodes for the consensus R, a typical basic amino acid of nuclear localization signals.

In the case of the S67P substitution approximately one third of the investigated human Hsmar1 coding regions, plus the chimpanzee clone used for the first set of mutagenesis contained the TCA triplet, coding for the consensus serine (S). On the contrary, the amino acid positions 201L and 219A are greatly underrepresented among the Hsmar1 copies of the human and the chimpanzee genomes, suggesting that these mutations might have been occurred relatively early in Hsmar1 evolution.

The amino acid 139L is not completely conserved within the transposases of the cecropia family; Hbmar1 contains a C at this position (FIG. 3). Still, the I139L mutation was carried out because within naturally occurring, and phylogenetically divergent mariner transposase subfamilies position 139 is almost exclusively taken by L. Notably, L139 is one of the landmarks of the predicted nonspecific DNA binding domain of mariner elements (Lampe et al., 1999, supra), suggesting that this amino acid is an absolute requirement of the mariner transposase activity (FIG. 4).

In sum, when creating the Hsmar1 transposon system, the apparently inactive majority-rule consensus sequence of Hsmar1 transposase gene published by Robertson and Zumpano (1997, supra) was further modified at five codons through a series of PCR mutagenesis. These amino acid substitutions were implied by comparative analyses of transposase coding regions of other naturally occurring mariner transposons.

In order to analyze the phylogenetic position of the modified transposase sequence a phylogenetic tree was generated from those genomic Hsmar1 transposase copies that were at least 90% complete in length compared to the consensus Hsmar1 amino acid sequence, the mutated transposase (Hsmar1-5mut), together with cecropia type transposases sequences (FIG. 4). The topology of the tree shows the expected pattern of idiosyncratic evolution of the genomic Hsmar1 copies (Robertson and Zumpano, 1997, supra), but more importantly it reveals that the hypothetical transposase sequence (Hsmar1-5mut) joins in to the root of the Hsmar1 cluster with the shortest branch. These results indicate that the engineered transposase gene represents an ancestral sequence of the present Hsmar1 genomic copies.

Figure 6:
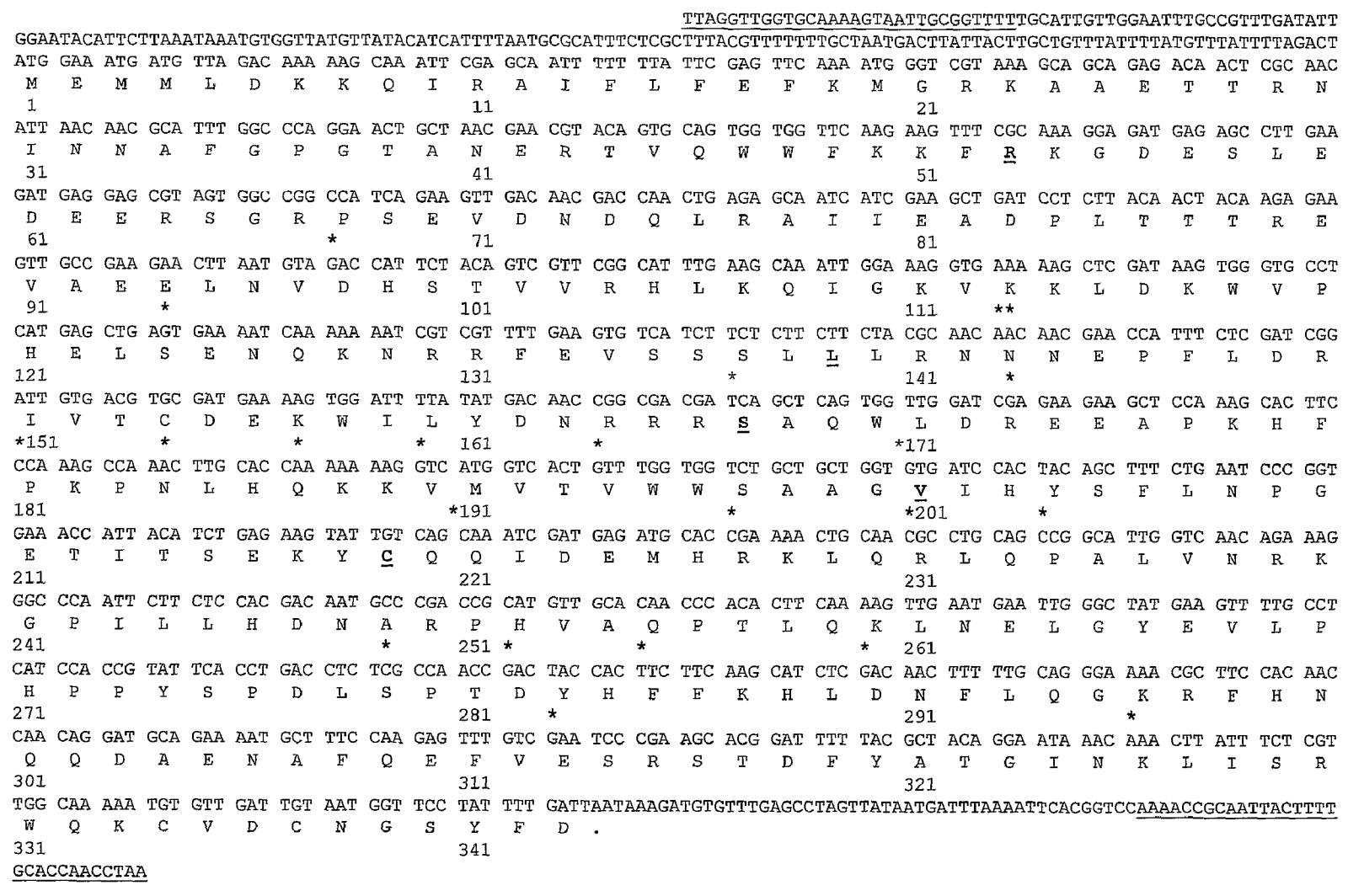

Hence it is likely that Hsmar1-5mut represents, or is very similar to, the sequence of the archaic transposase gene of the ancient mariner element that colonized the genome lineage of primates, approximately 50 million years ago (Robertson and Zumpano, 1997, supra) The reconstructed transposase gene was designated Hsmar1-Prime (Hsmar1-P, see FIG. 6, see also SEQ ID NOs: 1 and 2).

2. Transposition of Hsmar1-Prime in Human Cells

Figure 7:
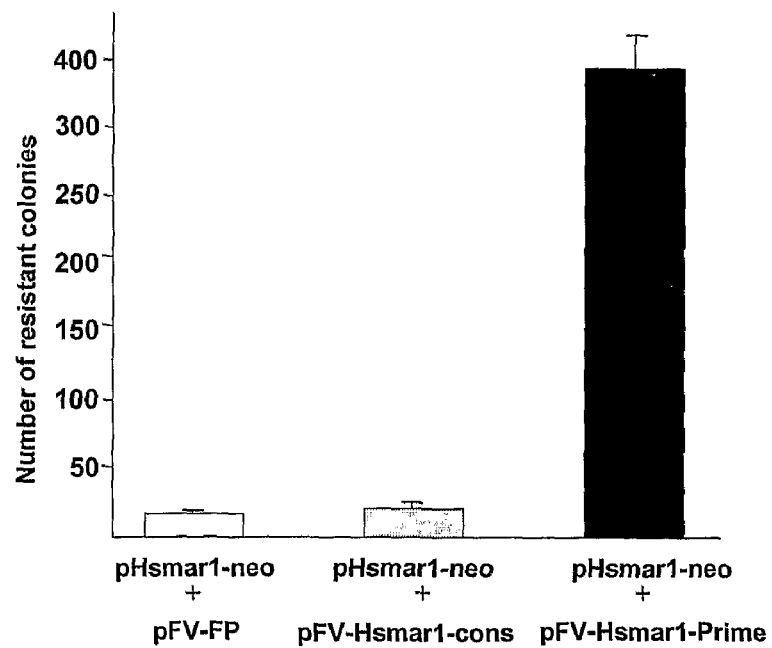
FIG. 7: Transpositional activity of Hsmar1 mutants in human HeLa cells.

Since the mutagenesis was done in multiple steps with three to five mutagenic primers per PCR reaction, the procedure generated several "premature" transposase gene versions. Each of these transposase ORFs was cloned into the pFV-4a expression vector and tested for transposition activity with the standard transposition assay in HeLa cells (FIG. 7A). None of the early version of transposases showed apparent transposition activity. However, we detected an approximately 20-fold increase in the number of G418 resistant colonies in the presence of the Hsmar1-P transposase version carrying all five predicted amino acid substitution (FIG. 7B). The available set of mutant transposase variants does not allow the investigation of the contribution of all mutated amino acid independently for transposase activity. However, the amino acids 139L and 219C turned out to be indispensable for transposase activity (FIG. 7). These results may indicate that most or all of the five amino acid positions in the transposases of the cecropia subfamily are indeed conserved because they are indispensable for transposition of these mariner elements. Taken together, the data demonstrate that we successfully combined the majority rule consensus of the Hsmar1 elements of the human genome with the phylogenetic analysis of related transposase genes to derive the first functional vertebrate mariner transposon system.

3. Molecular Characterization of Hsmar1-Prime Transposition

The significant increase in transgenesis frequency in the presence of the Hsmar1-P helper plasmid implied that the transposase can excise the transposons from the donor plasmids and integrate them into the host chromosomes. We used the transposon excision assay in order to characterize the excision step of the Hsmar1-P transposition. Low molecular weight DNA, which served as the template for the first PCRs was isolated three days after the cotransfection of the donor and helper plasmids from HeLa and CHO-K1 cells. The characteristic 260 bp PCR product, suggestive of the removal of the transposon from its donor plasmid was only obtained in the presence of the Hsmar1-P transposase (FIG. 8A). Sequencing of cloned PCR products revealed that Hsmar1 transposition machinery leaves a three bp long footprint at the site of transposon excision (FIG. 8B). Besides the standard footprint non-canonical excision derivatives were also detected. Among these we found "empty" transposon sites where the transposon footprint or flanking plasmid sequences were missing, most likely due to exonuclease activities before the religation of the empty donor plasmids took place. Similar results were obtained when excision sites of the Mos1 mariner element were analyzed in the *C. elegans* genome (Granger, L., Martin, E. & Segalat, L. (2004). Mos as a tool for genome-wide insertional mutagenesis in *Caenorhabditis elegans*: results of a pilot study. Nucleic Acids Res 32, e117).

In order to study the integration site preference of the excised Hsmar1 transposons, the donor plasmid was modified so that the IRs enclose a prokaryotic/eukaryotic promoter driven zeo cassette and a bacterial origin of replication. The resulting transposon makes it possible to perform plasmid rescue on genomic DNA containing chromosomally resident transposons. Sequencing of the genomic junctions of eight rescued transposon integrants from HeLa cells showed that Hsmar1 integrates into TA target nucleotides of the host genome (FIG. 8 C), which become duplicated at the integration site. Surprisingly, four out of eight cloned transposon insertions hit chromosome seven and other three integration events were identified from chromosome one. Approximately one third of the integration events hit introns of genes and no insertion was cloned from exons. These results indicate that Hsmar1 follows precise cut and paste transposition from plasmids to TA target nucleotides of human chromosomes.

4. Functionality of the Autonomous Hsmar1-Prime Transposon

In the following experiments it was shown that the expression of the transposase gene derived from a complete Mos1 mariner transposon preceded by about four kbp of *D. simulans* genomic DNA was sufficient to catalyze efficient autonomous transposition in chicken cells (Sherman, A., Dawson, A., Mather, C., Gilhooley, H., Li, Y., Mitchell, R., Finnegan, D. & Sang, H. (1998). Transposition of the *Drosophila* element mariner into the chicken germ line. Nat Biotechnol 16, 1050-3).

Figure 9:
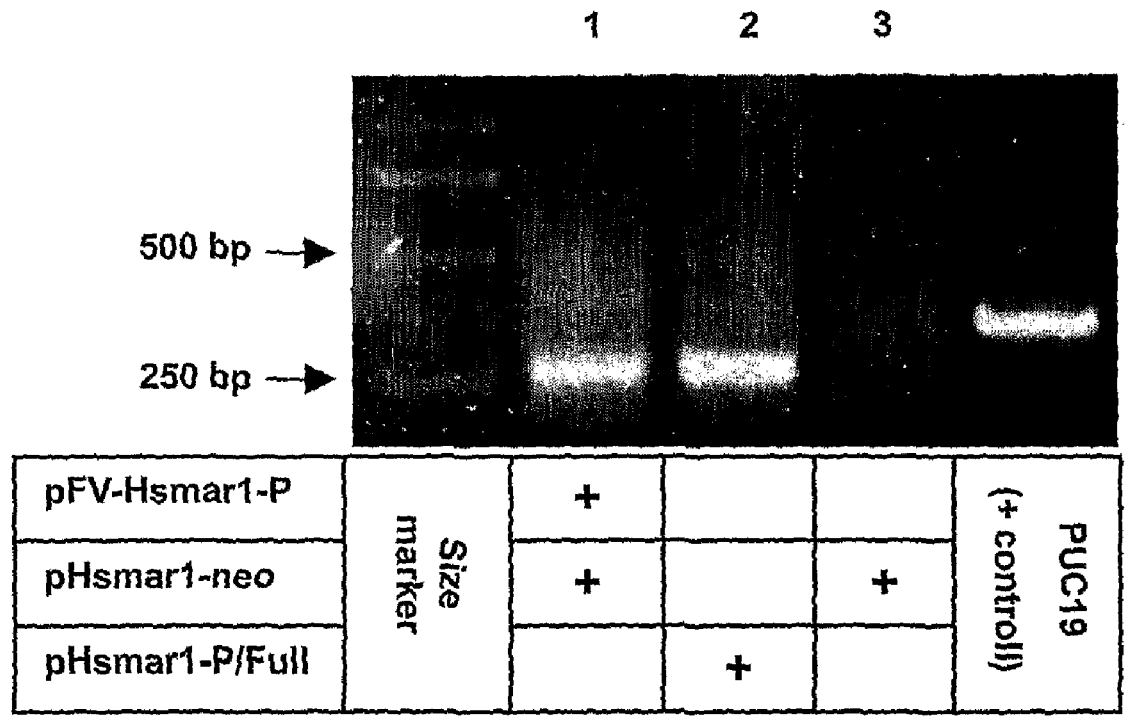
FIG. 9: Excision of the autonomous Hsmar1 in Chinese hamster cells.

In the previous transposition assays the Hsmar1 transposase gene was provided in trans to the corresponding transposons. To test weather the components of the Hsmar1-Prime transposon system can constitute an autonomous element, we subcloned the Hsmar1-P transposase gene between the corresponding IRs of the donor plasmid, to result in pHsmar1-P/Full. The structure of this transposon mimics that of the genomic Hsmar1 copies. pHsmar1-P/Full was transfected into CHO-K1 hamster cells and excision of the complete transposon was tested by the excision PCR assay (FIG. 9). The presence of the characteristic size PCR product was indicative of excision of the element from its host plasmid followed by successful excision site repair. In principle, it is possible that the hamster genome encodes for Hsmar1-like transposase(s) that could account for the removal of the transposon from its donor plasmid. To exclude the latter possibility DNA isolated from cells transfected with pHsmar1-neo only served as the control in the excision PCR assay. The absence of the characteristic size band in FIG. 9 lane 3 indicated that the removal of the transposon from the donor vector is strictly dependent on the presence of Hsmar1-P transposase.

In sum our results suggest that Hsmar1-Prime can transpose as an autonomous element. These data also imply that the Hsmar1-Prime transposon possess its own promoter sequences within the element, thus the expression of the transposase gene might not dependent on external promoter activities.

5. Results of the Experiments

We have reconstructed a functional Hsmar1 transposon of the human genome lineage, which is the first active mariner transposon from a vertebrate organism. Comparative phylogenetic analysis of transposases sequences of the cecropia subfamily of transposases suggested five amino acid replacements in the Hsmar1 transposase gene. Substitution of the deduced amino acids resulted in an active Hsmar1 transposase gene. The functional Hsmar1 transposon system was named Hsmar1-Prime, referring to the possibility that this element is identical, or very similar to the archaic transposon that entered a mammalian genome approximately 50 Myr ago (Robertson and Zumpano 1997, supra).

Transposition activity of the Hsmar1-P transposon system was measured in HeLa cells where the transfection of the functional transposase led to a twenty-fold increase in the number of the chromosomally integrated Hsmar1-neo transposons (FIG. 7). Several naturally occurring and hyperactive versions of the Mos1, Tc1, Tc3 and Himar1 transposases alongside with the Sleeping Beauty transposon system have been compared for jumping activity in HeLa cells (Fischer, S. E., Wienholds, E. & Plasterk, R. H. (2001). Regulated transposition of a fish transposon in the mouse germ line. Proc Natl Acad Sci USA 98, 6759-64). In these experiments the transpositional activity of SB was, on average, about 22-fold higher than that of the invertebrate Tc1/mariner elements. Similarly, the transposition efficiency of Hsmar1-P in HeLa cell line showed that it has an order of magnitude higher activity than any of the tested invertebrate elements.

By the inspection of the excision and integration sites I proved that Hsmar1-P performs precise cut-and-paste transposition in human HeLa cells (FIG. 8). The three bp long transposon footprint at the site of excision implies that the transposon cleavage, which exposes the 3' OH group for the strand transfer reactions is generated three base pairs within the transposon IRs. These data are in consistence with those obtained with Mos1 and Himar1 elements (Chandler and Mahillon in Mobile DNA II, p. 316, Ed. Craig et al., 2002). Sequence analyses of the genomic insertion sites in human cells did not reveal any obvious consensus sequence other than the expected TA target pair (FIG. 8 C). The distribution of Mos1 mariner and Sleeping Beauty transposon integrants was uniform in C. elegans and human HeLa chromosomes, respectively (Granger et al., 2004 (supra); Vigdal, T. J., Kaufman, C. D., Izsvak, Z., Voytas, D. F. & Ivics, Z. (2002). Common physical properties of DNA affecting target site selection of sleeping beauty and other Tc1/mariner transposons. J Mol Biol 323, 441-52), On the contrary, 50% of all Hsmar1 de novo integration events were identified from chromosome seven and 37% hit chromosome one (FIG. 8). The apparent preference of Hsmar1 to integrate into these chromosomes should be further investigated by analyzing a large number of transposon insertions.

6. Materials and Methods 6.1 Open Reading Frame (ORF) Trapping

The primers Hsmar1-F (5'GACTGCGGCCGCAGAC-TATGGAAATGATGTTAGACAAAAAGC) (SEQ ID NO:8) and 5'AAAATAGGAACCATTACAATCAAC (SEQ ID NO:9) were used to amplify Hsmar1 transposase coding regions from human and chimpanzee genomic DNA isolated from HeLa and COS cells, respectively. The PCR products were cloned into the NotI/SmaI sites of pCMVβFUSa (see above).

6.2 Cell Culture and Transfection

HeLa and CHO-K1 cells were maintained in DMEM; FHM, A6 and PAC2 cells were cultured in L-15 medium containing 10% fetal bovine serum. Transposition assays were done as described (Ivics, Z., Hackett, P. B., Plasterk, R. H. & Izsvak, Z. (1997). Molecular reconstruction of Sleeping Beauty, a Tc1-like transposon from fish, and its transposition in human cells. Cell 91, 501-10). Briefly, $3 \times 10^5$ cells were transfected with 100 ng of each the transposon donor plasmid and the transposase-expressing helper plasmid using FUGENE6 transfection reagent (Roche). Two days post-transfection, the cells were replated and selected in 400 μg/ml G418 for PAC2 and CHO-K1 cells, and 1.4 mg/ml G418 for HeLa, FHM and A6 cells. After two weeks of selection, the G418-resistant colonies were either stained and counted, or picked and expanded to individual cultures.

6.3 Transposon Excision Assays

Cultured cells were transfected with helper plasmids and/or the corresponding donor plasmids. Low molecular weight DNA was prepared two days post-transfection, using QiaPrep Spin column protocol supplemented with proteinase K (Qiagen). 1.mu.l of the eluted extracts was used as template for PCR with primers 5'CAGTAAGAGAATTATGCAGT-GCTGCC (SEQ ID NO:10) and 5'CCTCTGACACATGC AGCTCCCGG (SEQ ID NO:11). A 1 μl aliquot of the 30 μl PCR reaction was further amplified with primers 5'TCTTTC-CTGCGTTATCCCCTGATTC (SEQ ID NO:12) and 5'TCA-CAAGCTTGTC TGTAAGCGG (SEQ ID NO:13). 1 μl 100-fold diluted aliquot of the second PCR was further amplified with primers 5'GCGAAAGGGGGATGTGCTGCAAGG (SEQ ID NO:14) and 5'CAGCTGGCACGACAGGTTTC-CCG (SEQ ID NO:15). The first two PCRs were 30 cycles of 94° C. 30 s, 65° C. 30 s, and 72° C. 1 min; the third PCR was 30 cycles of 94° C. 30 s, 65° C. 30 s, and 72° C. 30 s, using standard PCR reaction conditions in 50 μl with 10 pmol of forward and reverse primer each. To analyze excision footprints the excision PCR products were isolated from gels and cloned using the pGEM Easy Kit (Stratagene) before sequencing.

6.4 Plasmid Rescue of Integrated Hsmar1 Transposons

For plasmid rescue, genomic DNA was isolated from either pooled, or expanded individual zeocin- or G418/zeocin double-resistant HeLa clones. Approximately 10 μg DNA was digested with SpeI, which does not cut within the gene trap transposon in pHsmar1/GT-zeo. The fragments were ethanol precipitated and self-ligated using T4 DNA ligase (New England Biolabs), under dilute conditions and electroporated into DH10B bacteria, which were than selected on plates containing 50 μg/ml zeocin. Plasmids DNA isolated from resistant colonies were sequenced using IR-specific primers; for the Hsmar1 transposons: 5'ATGATGTATAA-CATAACCACATTTATTTAAGAATGTATTC (SEQ ID NO:16) and 5'TAAAG ATGTGTTTGAGCCTAGTTATAAT-GATTTAAAATTCACGGTCCAAA (SEQ ID NO:17) specific for the 5' and 3' IRs, respectively.

6.5 PCR Mutagenesis of the Hsmar1 Transposase; and Hsmar1 Plasmids.

pCMVβFUSa containing ORF No. 1 derived from chimpanzee served as template in a PCR to amplify the transposase gene with the primers Hsmar1-F and 5'CTGAAC-TAGTCTAATCAAAATAGGAACCATTACAATCAAC (SEQ ID NO:18). The PCR product was cloned into the NotI-SpeI sites (underlined) of pFV-4a (Liu et al., 1997) to perform the first round of mutagenesis. The rest of the mutagenesis reactions were done after subcloning the transposase coding sequence into SacII-SpeI site of pBluescript SK+ (Stratagene). The PCR reactions were performed in the presence of 3-5 mutagenic primers per reactions with Multi-Change Site Directed-Mutagenesis Kit (Stratagene) following the manufacturer's instructions. The table below lists the mutagenic primers. Majority of the primers were used to obtain the consensus amino acid sequence of the Hsmar1 transposase gene predicted by Robertson and Zumpano (1997, supra). Five additional primers (underlined) were used to result in the Hsmar1-Prime transposase gene.

| Mutagenic primer | Mutation(s) in SEQ ID NO: 1 |
|---|---|
| 5'GCTCCAAAGCACTTCCCAAAGCCAATCTTGCACC (SEQ ID NO: 19) | S181P |
| 5'TGAGAAGTATGCTCAGCAAATCGATGAGATGCACC (SEQ ID NO: 20) | E221Q |
| 5'CAACCGACTACCACTTCTTCAAGCATCTCGACAAC (SEQ ID NO: 21) | I285F |
| 5'ACAACCGGCGACGACCAGCTCAGTGGTTGGATC (SEQ ID NO: 22) | S167P |
| 5'CAAAGCCAATCTTGCACCAAAAAAAGGTCATGGTCACTGTTTGGTGG (SEQ ID NO: 23) | I184N + P187Q |
| 5'CCGAAAACTGCAACGCCTGCAGCCGGCATTGGTCAACAGAAAGG (SEQ ID NO: 24) | H231R + L234P |
| 5'CGTATTCACCTGACCTCTCGCCAACCGACTACCACATCTTCAAGC (SEQ ID NO: 25) | L279S + N282D |
| 5'GAAGAACTTAATGTAGACCATTCTACAGTCGTTCGGC (SEQ ID NO: 26) | N98D |
| 5'CTTATTCTACGCAACAACAACGAACCATTTCTCGATCG (SEQ ID NO: 27) | R143N |
| 5'GTGCCTCATGAGCTGAGTGAAAATCAAAAAAATCGTCG (SEQ ID NO: 28) | T124S |
| 5'CAGTGGTTGGATCGAGAAGAAGCTCCAAAGCACTTC (SEQ ID NO: 29) | Q173R |
| 5'AAAGGTCATGGTCACTGTTTGGTGGTCTGCTGCTGG (SEQ ID NO: 30) | I190V + I194V |
| 5'TCTGCTGCTGGTCTGATCCACTACAGCTTTC (SEQ ID NO: 31) | V201L |
| 5'TCGATGAGATGCACCGAAAACTGCAACACCTGCAG (SEQ ID NO: 32) | Q227R |
| 5'CATCTTCAAGCATCTCGACAACTTTTTGCAGGG (SEQ ID NO: 33) | N290D |
| 5'TTACGCTACAGGAATAAACAAACTTATTTCTCGTTGGC (SEQ ID NO: 34) | Q326K |
| 5'CTTTCCAAGAGTTTGTCGAATCCCGAAGCACGG (SEQ ID NO: 35) | K313E |
| 5'GTGGTTCAAGAAGTTTCGCAAAGGAGATGAGAGCCTTGAAG (SEQ ID NO: 36) | C53R |
| 5'ACAACCGGCGACGATCAGCTCAGTGGTTGGATCGAG (SEQ ID NO: 37) | P167S |
| 5'TCTGCTGCTGGTGTGATCCACTACAGCTTTCTGAATCCC (SEQ ID NO: 38) | L201V |
| 5'CCATTACATCTGAGAAGTATTGTCAGCAAATCGATGAGATGCACC (SEQ ID NO: 39) | A219C |
| 5'AAGTGTCATCTTCTCTTCTTCTACGCAACAACAACGAACCATTTC (SEQ ID NO: 40) | I139L |

Following the mutagenesis the transposase versions were cloned into the SacII-SpeI or the NotI-SpeI sites of pFV4a to test them for activity in transposition assays.

To obtain the Hsmar1 transposon donor plasmid the Klenow-filled EcoRI-BamHI fragment of pRC/CMV (Invitrogen), containing the SV40 promoter/enhancer, neo gene and the SV40 poly-A signal was cloned into the SmaI site of pUC19 to gain pUC/neo. The left and right Hsmar1 IRs were oligo-assembled as described in Stemmer et al., (1995) and cloned into the EcoRI-KpnI and XbaI-HindIII sites of pUC/neo. The resulting plasmid was called pHsmar1/neo.

pHsmar1/PR-zeo was cloned by replacing the KpnI-XbaI fragment of pHsmar1/neo by a prokaryotic/eukaryotic promoter driven zeo gene and a bacterial origin of replication.

pHsmar1/Full was derived by replacing the KpnI-XbaI fragment of pHsmar1/neo by the Klenow-blunted SacII-SpeI fragment of pFV-Hsmar1-Prime containing the functional transposase gene.

6.6 Phylogenetic Analysis

To investigate the phylogenetic position of Hsmar1-Prime among human Hsmar1 copies, transposase protein sequence of Csmar1 was used to collect Hsmar1 elements in the human genome. First, we applied TBLASTN (Altschul et al., (1997), Nucleic Acids Res 25, 3389-402) to search for potential homologues in the translated chromosomal sequences of *Homo sapiens* at an E-value cutoff of $10^{-5}$. Second, only hits with the following criteria were retained for further analysis: i) alignment covering at least 90% of the query Csmar1 protein, ii) less than 10% gaps in the alignment, and iii) sequence identity more than 30%. This procedure resulted in 56 human sequences, which were aligned by T-Coffee using default settings (Notredame et al., (2000); J Mol Biol 302, 205-17). Phylogeny of these mariner elements was reconstructed using the maximum likelihood method implemented in PhyML (Guindon and Gascuel, 2003, Syst Biol 52, 696-704), rooted to the invertebrate members of the cecropia transposase subfamily and displayed in TreeView 1.6.6 (Roderik, 2000)

The invention claimed is:

1. An isolated nucleic acid comprising a nucleic acid sequence selected from the group consisting of:
   a) a nucleic acid sequence encoding a human mariner transposase protein sequence having at least 95% sequence identity to SEQ ID NO: 1, wherein the following amino acids with respect to SEQ ID NO: 1 remain unaltered:
      ii) Arginine at amino acid position 53;
      ii) Lysine at amino acid position 139;
      iii) Serine at amino acid position 167;
      iv) Valine at amino acid position 201; and
      v) Cysteine at amino acid position 219; and
   b) a nucleic acid sequence as shown by SEQ ID NO: 2.

2. The nucleic acid of claim 1, wherein the nucleic acid is RNA or DNA.

3. A plasmid or a recombinant viral vector comprising the isolated nucleic acid of claim 1.

4. The nucleic acid of claim 1 wherein the nucleic acid additionally comprises at least a portion of an open reading frame.

5. The nucleic acid of claim 1 wherein the nucleic acid additionally comprises at least a regulatory region of a gene.

6. The nucleic acid of claim 5, wherein the regulatory region is a transcriptional regulatory region.

7. The nucleic acid of claim 6 wherein the regulatory region is selected from the group consisting of a promoter, an enhancer, a silencer, a locus-control region, and a border element.

8. A transposon comprising an isolated nucleic acid comprising the nucleic acid sequence of claim 1 positioned between at least two repeats, wherein the repeats can bind to the human mariner transposase protein encoded by the nucleic acid of claim 1, wherein the transposon is capable of inserting into DNA of a cell.

9. The transposon of claim 8 wherein the transposon further comprises a nucleic acid encoding marker protein selected from the group consisting of green fluorescent protein (GFP), chloramphenicol acetyltransferase (CAT), a growth hormone, [beta]-galactosidase (lacZ), luciferase (LUC), and insulin-like growth factor (IGFs).

10. A plasmid comprising the transposon of claim 8.

11. The transposon of claim 8 wherein the transposon further comprises at least a portion of an open reading frame.

12. The transposon of claim 8 wherein the transposon further comprises at least one expression control region.

13. The transposon of claim 12 wherein the expression control region is selected from the group consisting of a promoter, an enhancer and a silencer.

14. The transposon of claim 8 wherein the transposon further comprises a promoter operably linked to at least a portion of an open reading frame.

15. The transposon of claim 8 wherein the cell is obtained from an animal.

16. The transposon of claim 15 wherein the cell is obtained from a vertebrate or an invertebrate.

17. The transposon of claim 16 wherein the invertebrate is selected from a crustacean or a mollusk.

18. The transposon of claim 16 wherein the vertebrate is selected from the group consisting of a fish, a bird, and a mammal.

19. The transposon of claim 18 wherein the mammal is selected from the group consisting of mice, ungulates, sheep, swine, and humans.

20. The transposon of claim 8 wherein the DNA of a cell is selected from the group consisting of chromosomal DNA, an episome, and a plasmid.

21. The transposon of claim 8 wherein at least one of the repeats comprises the sequence of SEQ ID NO:4 or SEQ ID NO:5.

22. The transposon of claim 8 wherein the transposon comprises the sequence of SEQ ID NO:3.

23. The transposon of claim 8 wherein at least one of the repeats comprises at least one direct repeat.

24. An isolated cell comprising the transposon of claim 8 or the nucleic acid of claim 1.

25. An isolated cell producing proteins encoded by the transposon of claim 8 or the nucleic acid of claim 1.

26. An isolated nucleic acid comprising the nucleic acid sequence according to claim 1 having at least 98% sequence identity to SEQ ID NO: 1.

* * * * *